United States Patent
Tokunaga et al.

(10) Patent No.: US 9,710,146 B2
(45) Date of Patent: Jul. 18, 2017

(54) SYSTEM AND METHOD FOR IMAGE DISPLAY CONTROL

(75) Inventors: Tatsuya Tokunaga, Tokyo (JP); Hiroki Taniguchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 593 days.

(21) Appl. No.: 14/241,520

(22) PCT Filed: Aug. 7, 2012

(86) PCT No.: PCT/JP2012/070112
§ 371 (c)(1),
(2), (4) Date: Mar. 26, 2014

(87) PCT Pub. No.: WO2013/046940
PCT Pub. Date: Apr. 4, 2013

(65) Prior Publication Data
US 2014/0229890 A1    Aug. 14, 2014

(30) Foreign Application Priority Data
Sep. 29, 2011    (JP) ................................. 2011-214904

(51) Int. Cl.
*G06F 3/0485* (2013.01)
*G09G 5/34* (2006.01)
(Continued)

(52) U.S. Cl.
CPC .......... *G06F 3/04855* (2013.01); *A61B 5/742* (2013.01); *A61B 6/465* (2013.01);
(Continued)

(58) Field of Classification Search
CPC ............... G06F 3/04855; G06F 3/0485; G06F 2203/04806; G09G 5/34; G09G 2380/08;
(Continued)

(56) References Cited

U.S. PATENT DOCUMENTS

| 5,418,549 A | 5/1995 | Anderson et al. |
| 2002/0063737 A1* | 5/2002 | Feig ..................... G06F 3/04847 715/786 |
| 2002/0109728 A1* | 8/2002 | Tiongson ............ G06F 3/04855 715/786 |
| 2002/0109735 A1* | 8/2002 | Chang .................... A61B 6/463 715/853 |
| 2008/0297536 A1* | 12/2008 | Matsuno ............... G06F 3/0485 345/684 |
| 2009/0282362 A1 | 11/2009 | Matsumoto |

(Continued)

FOREIGN PATENT DOCUMENTS

| JP | 5-174068 | 7/1993 |
| JP | H 07-098643 | 4/1995 |

(Continued)

OTHER PUBLICATIONS

JP Office Action mailed Mar. 3, 2015 in JP Patent Application No. 2013-536042.

*Primary Examiner* — Jennifer To
*Assistant Examiner* — John Repsher, III
(74) *Attorney, Agent, or Firm* — Baker Botts L.L.P.

(57) ABSTRACT

Provided is a technology that supports a user in easily selecting an image of interest from among a large quantity of continuous images while making the best use of characteristics of a scroll function. The technology prepares a first scroll area that receives an indication for sequentially scrolling images to be displayed on a display screen among the large quantity of continuous images by a predetermined first amount of a scroll; and a second scroll area that receives an indication for sequentially scrolling the images by the amount of a scroll smaller than the first amount of a scroll, in a case where the number of the continuous images is greater than the maximum number of designatable positions of the first scroll area.

14 Claims, 19 Drawing Sheets

(51) Int. Cl.
*A61B 6/00* (2006.01)
*G09G 5/377* (2006.01)
*A61B 5/00* (2006.01)

(52) U.S. Cl.
CPC ............ *G06F 3/0485* (2013.01); *G09G 5/34* (2013.01); *A61B 5/7435* (2013.01); *G06F 2203/04806* (2013.01); *G09G 5/377* (2013.01); *G09G 2380/08* (2013.01)

(58) Field of Classification Search
CPC ........ G09G 5/377; A61B 5/742; A61B 6/465; A61B 6/00; A61B 5/7435
USPC ....................................................... 715/786
See application file for complete search history.

(56) References Cited

U.S. PATENT DOCUMENTS

2014/0033099 A1\* 1/2014 Treitman ............ G06F 3/04855 715/768

FOREIGN PATENT DOCUMENTS

| | | |
|---|---|---|
| JP | 2001-202176 | 7/2001 |
| JP | 2004-62644 | 2/2004 |
| JP | 2005-56302 | 3/2005 |
| JP | 2006-285471 A | 10/2006 |
| JP | 2009-295147 | 12/2009 |
| JP | 2010-234068 | 10/2010 |

\* cited by examiner

[FIG.1]
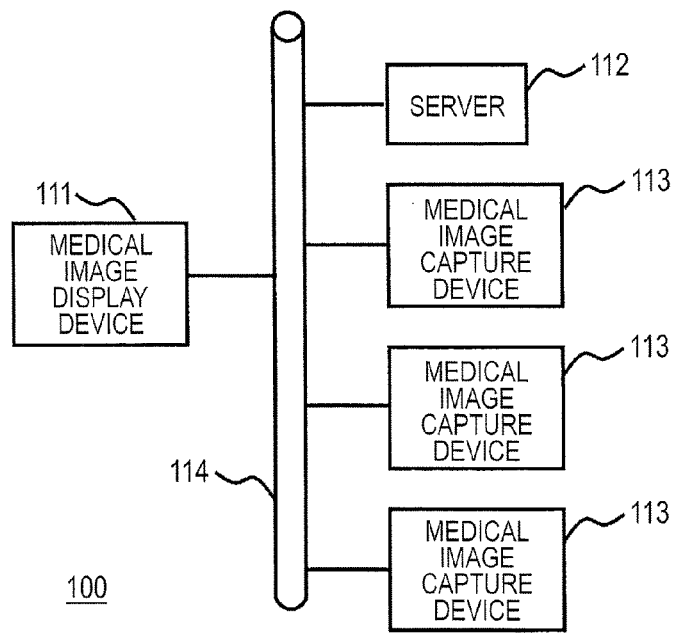
(a)
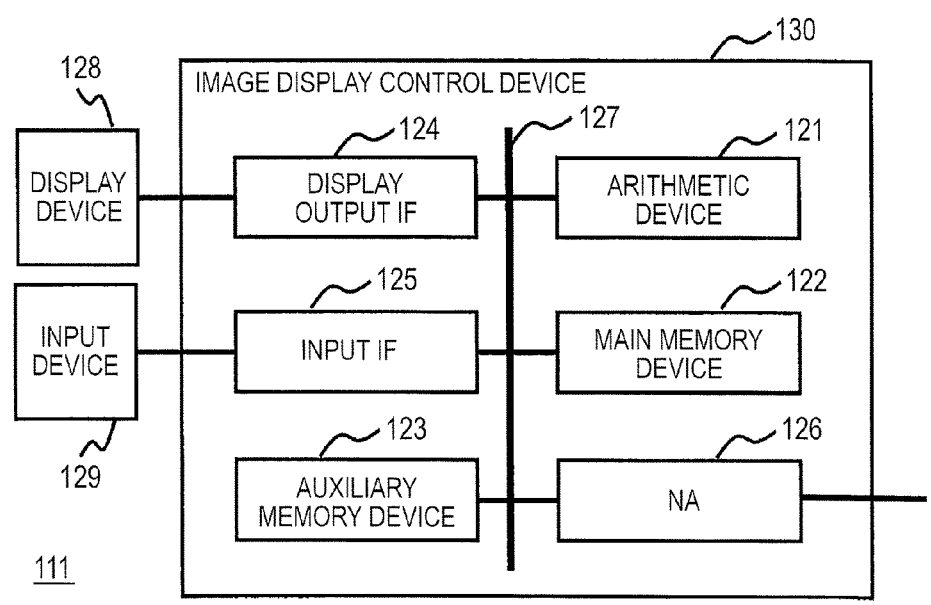
(b)

[FIG.2]
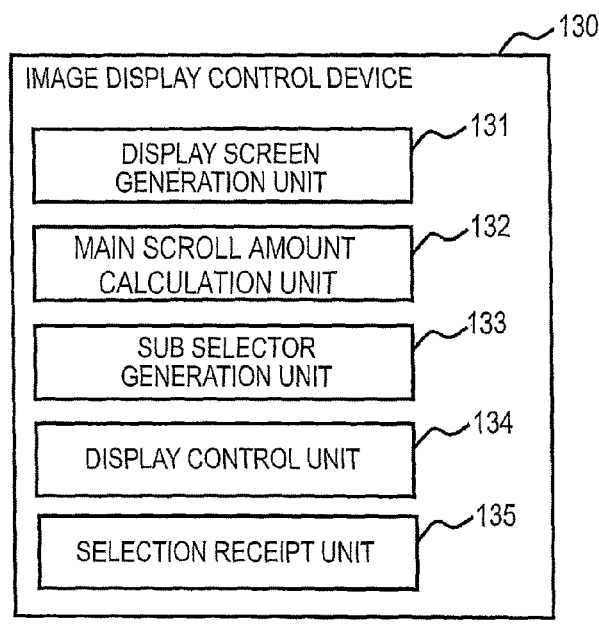
[FIG.3]
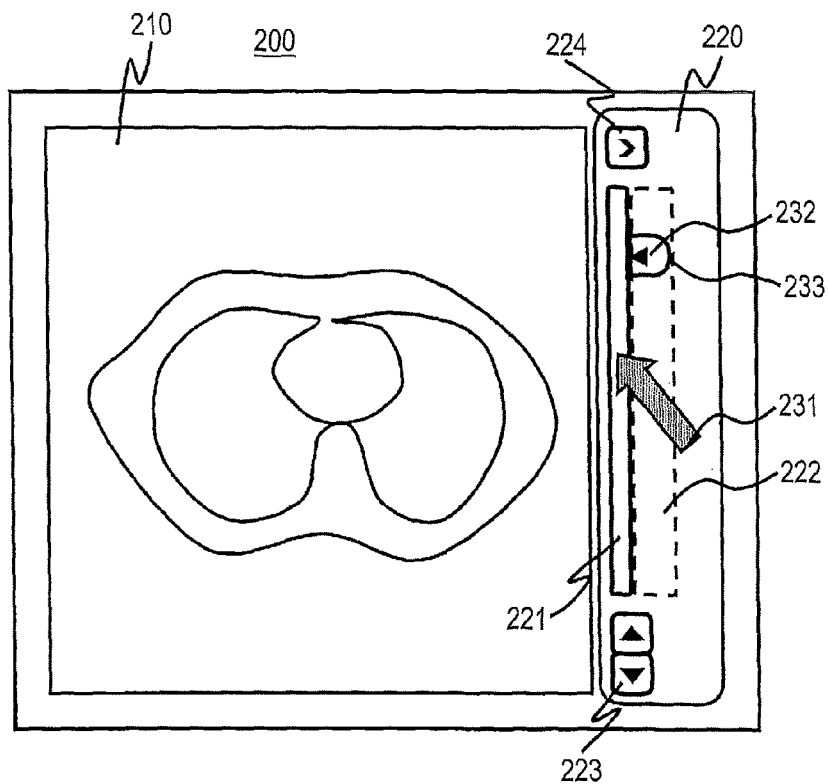

[FIG.4]
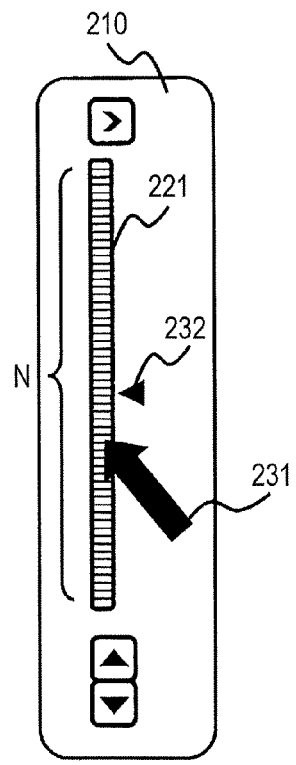
(a)
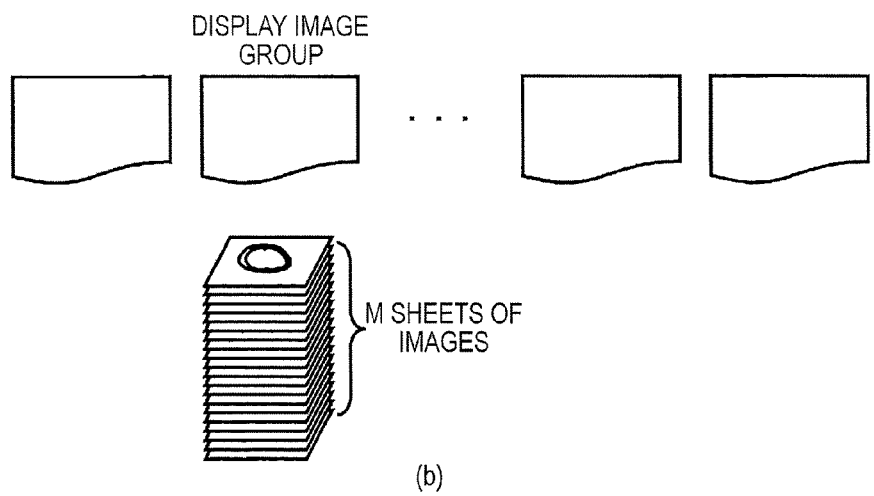
(b)

[FIG.5]
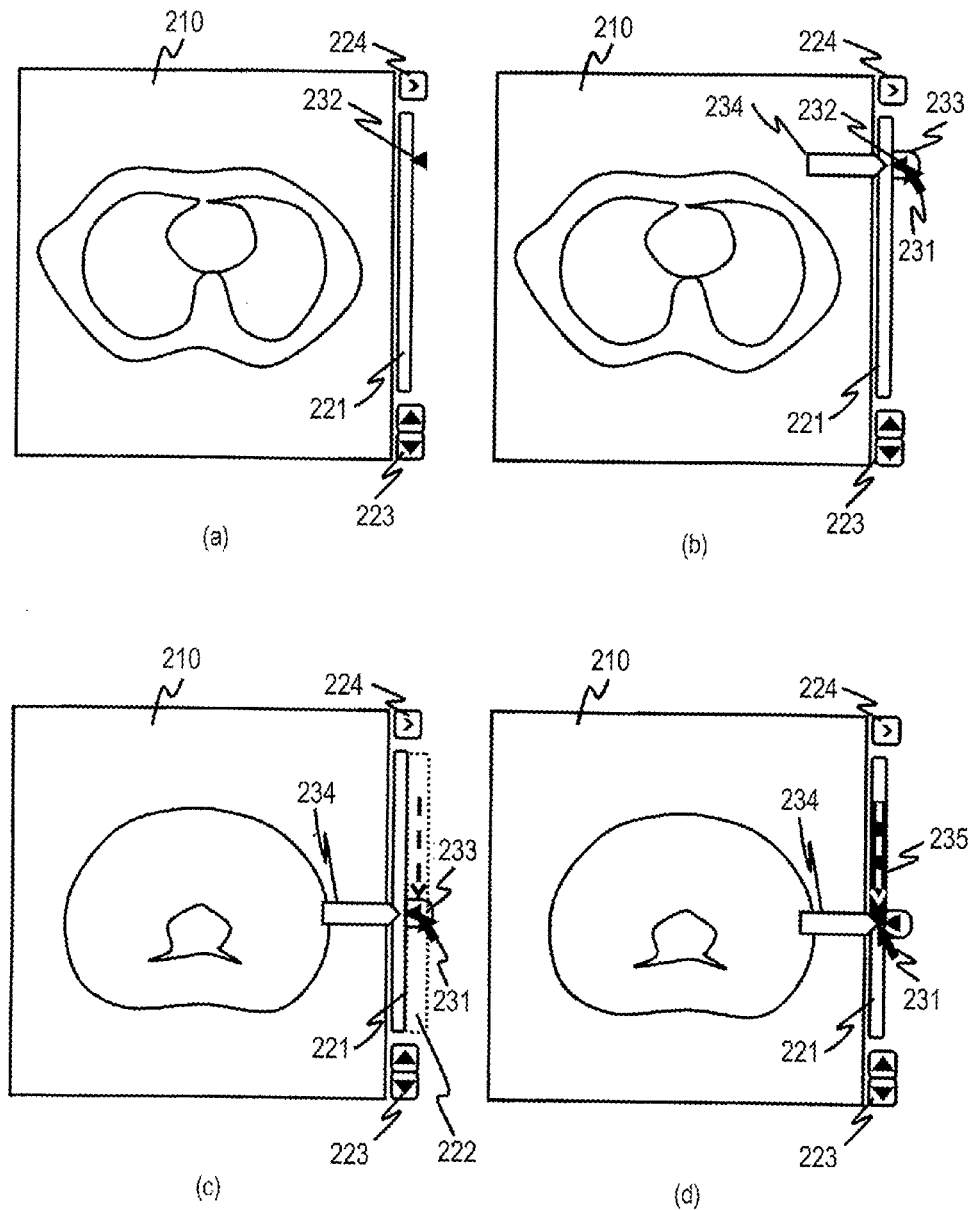

[FIG.6]
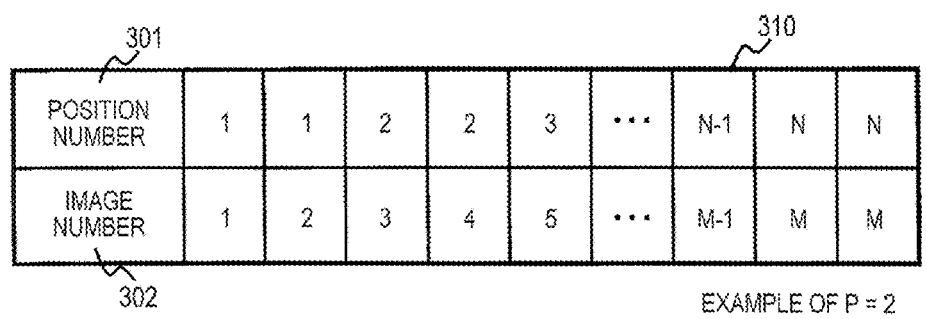
(a)
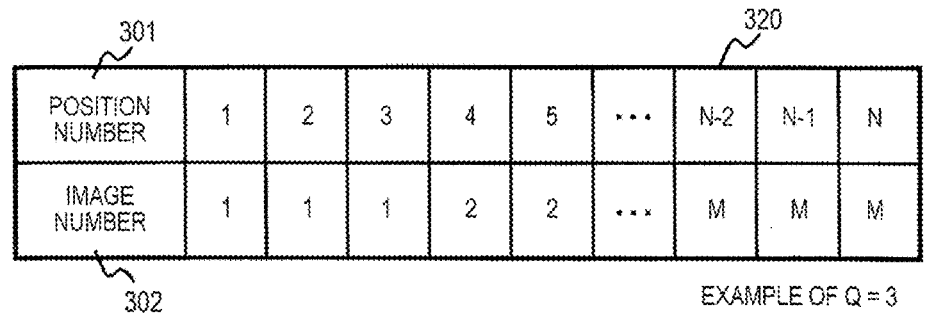
(b)

[FIG.7]
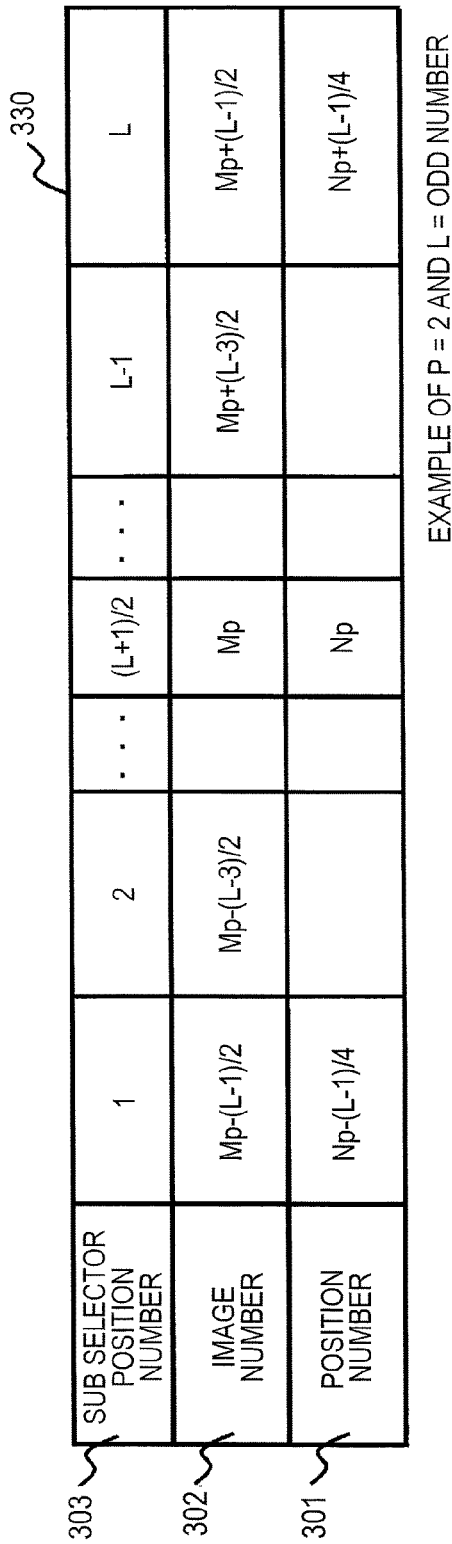

[FIG.8]
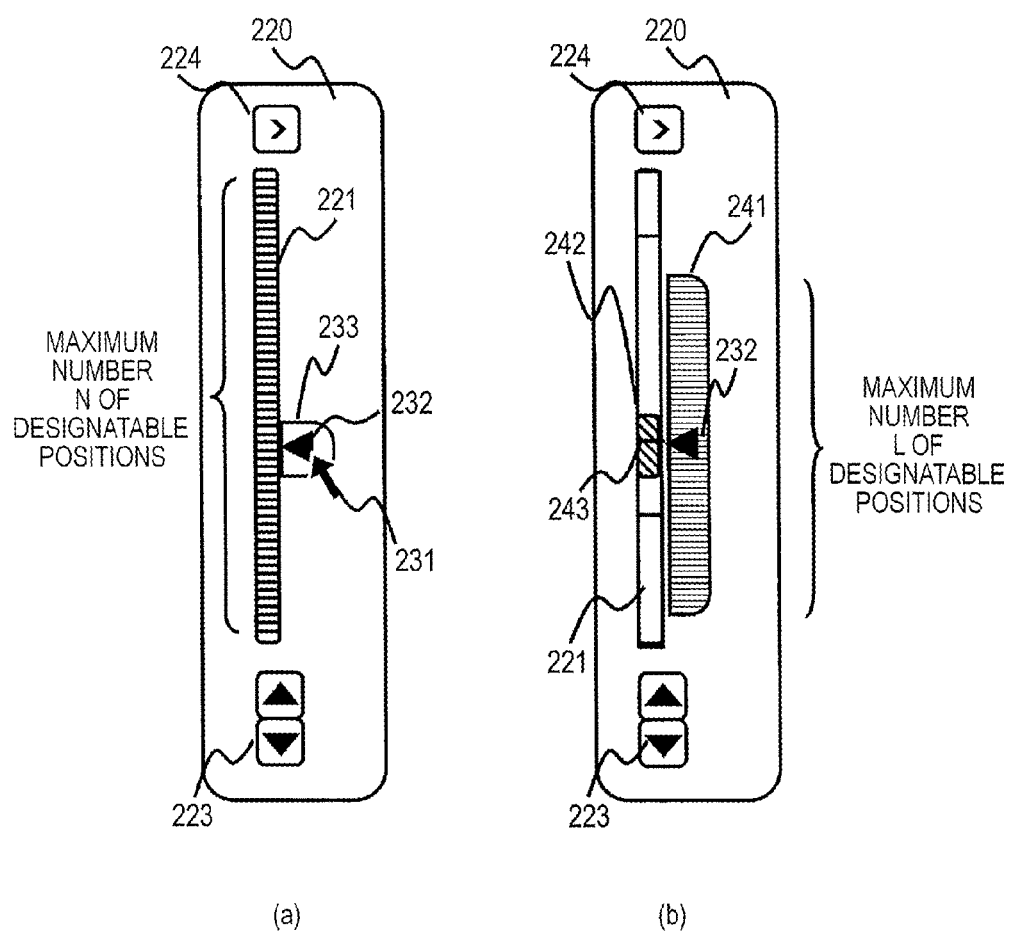
(a) (b)

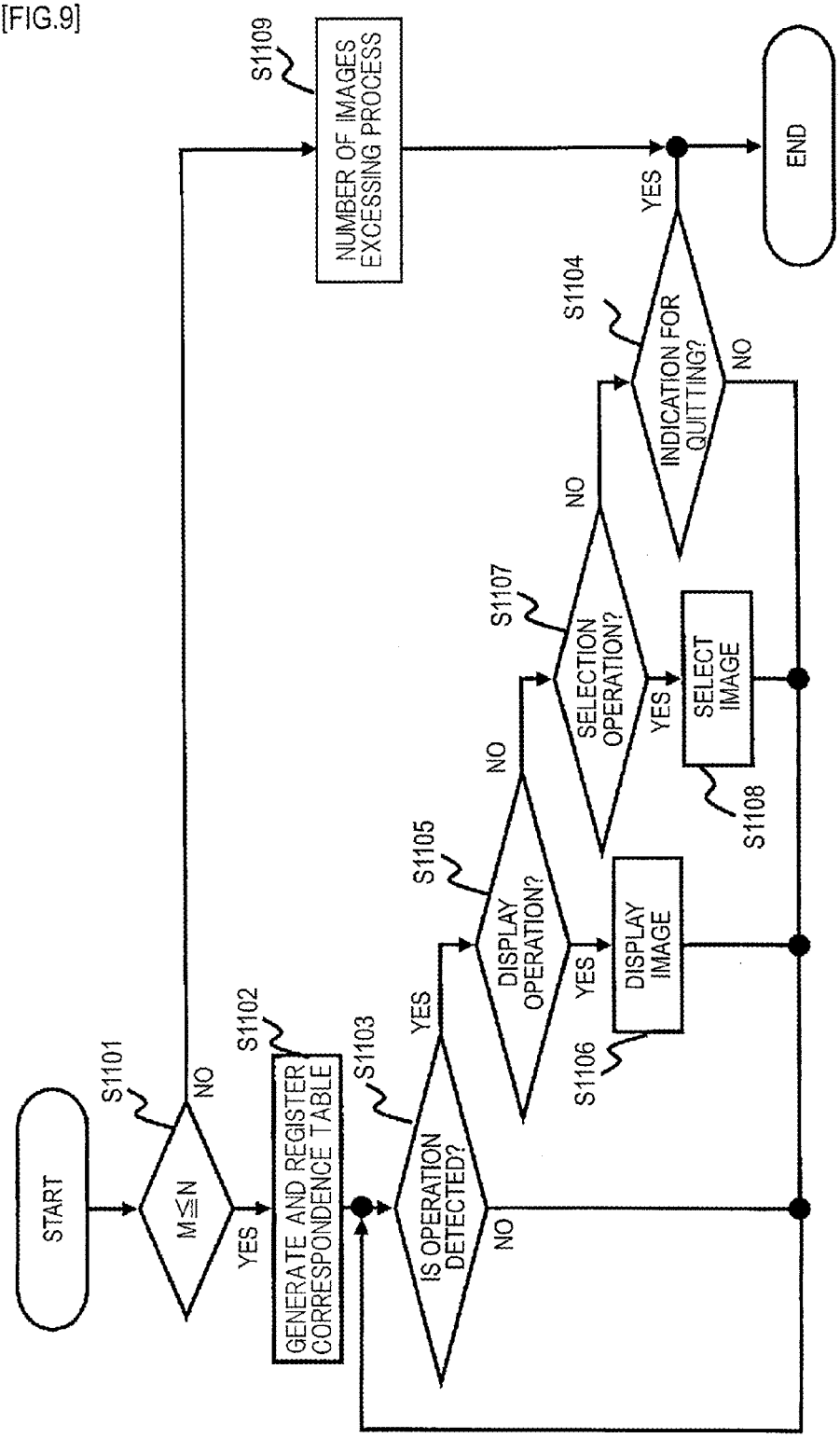
[FIG.9]

[FIG.10]
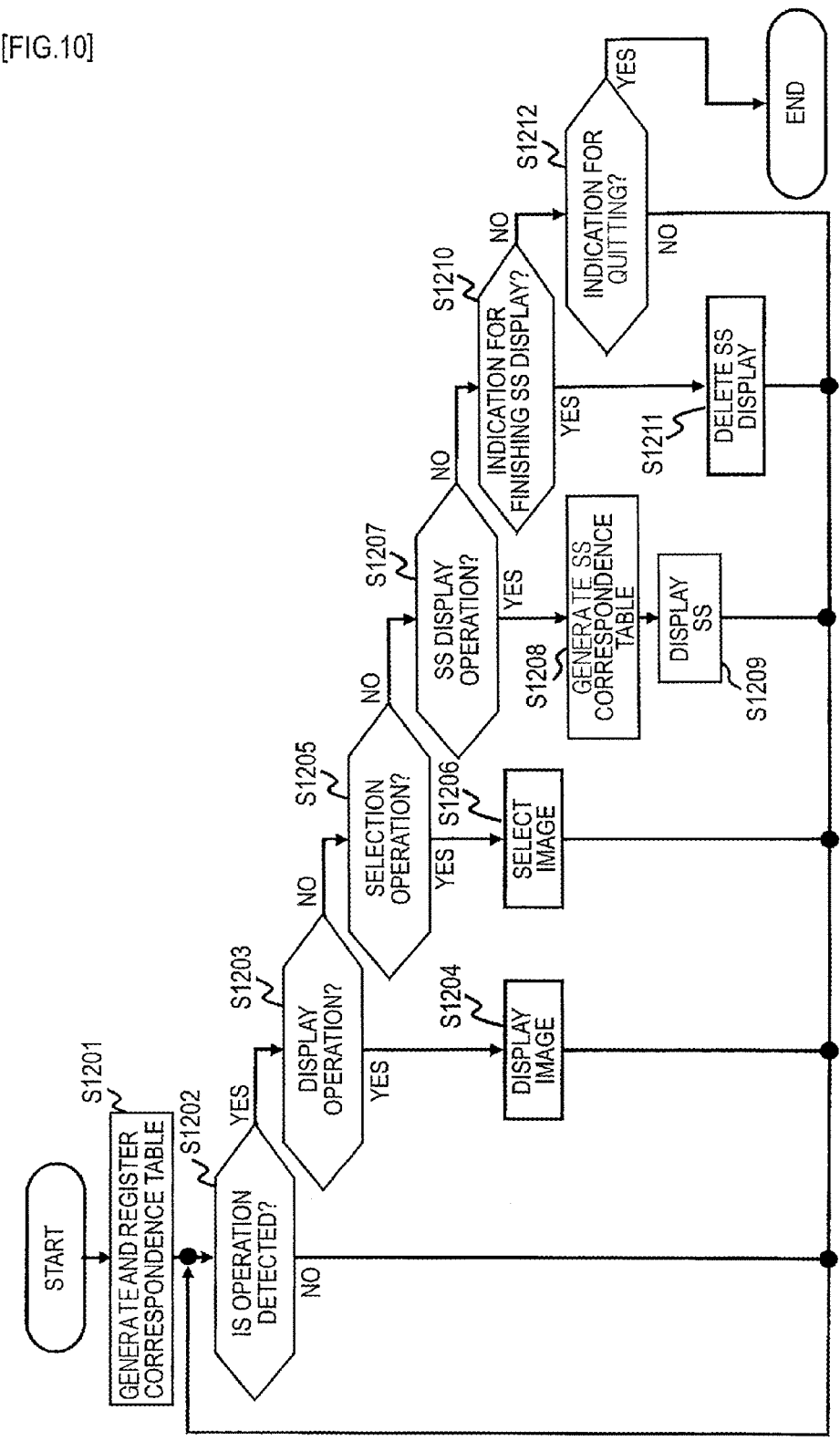

[FIG.11]
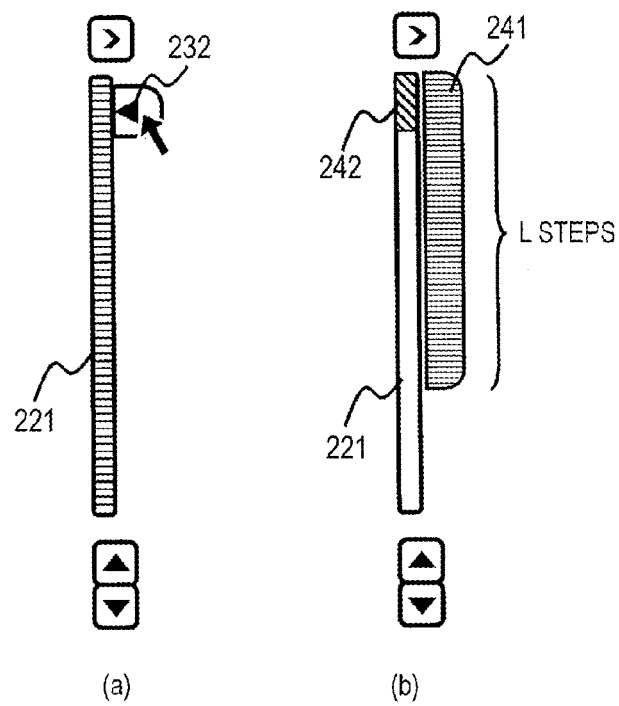
(a)  (b)
[FIG.12]
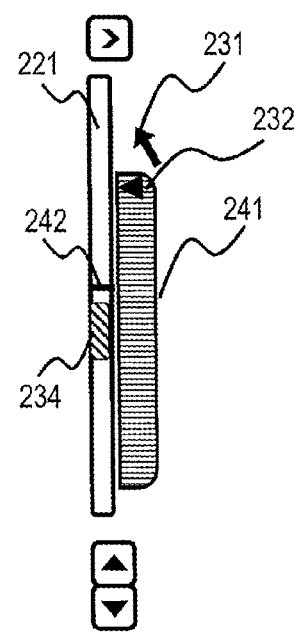

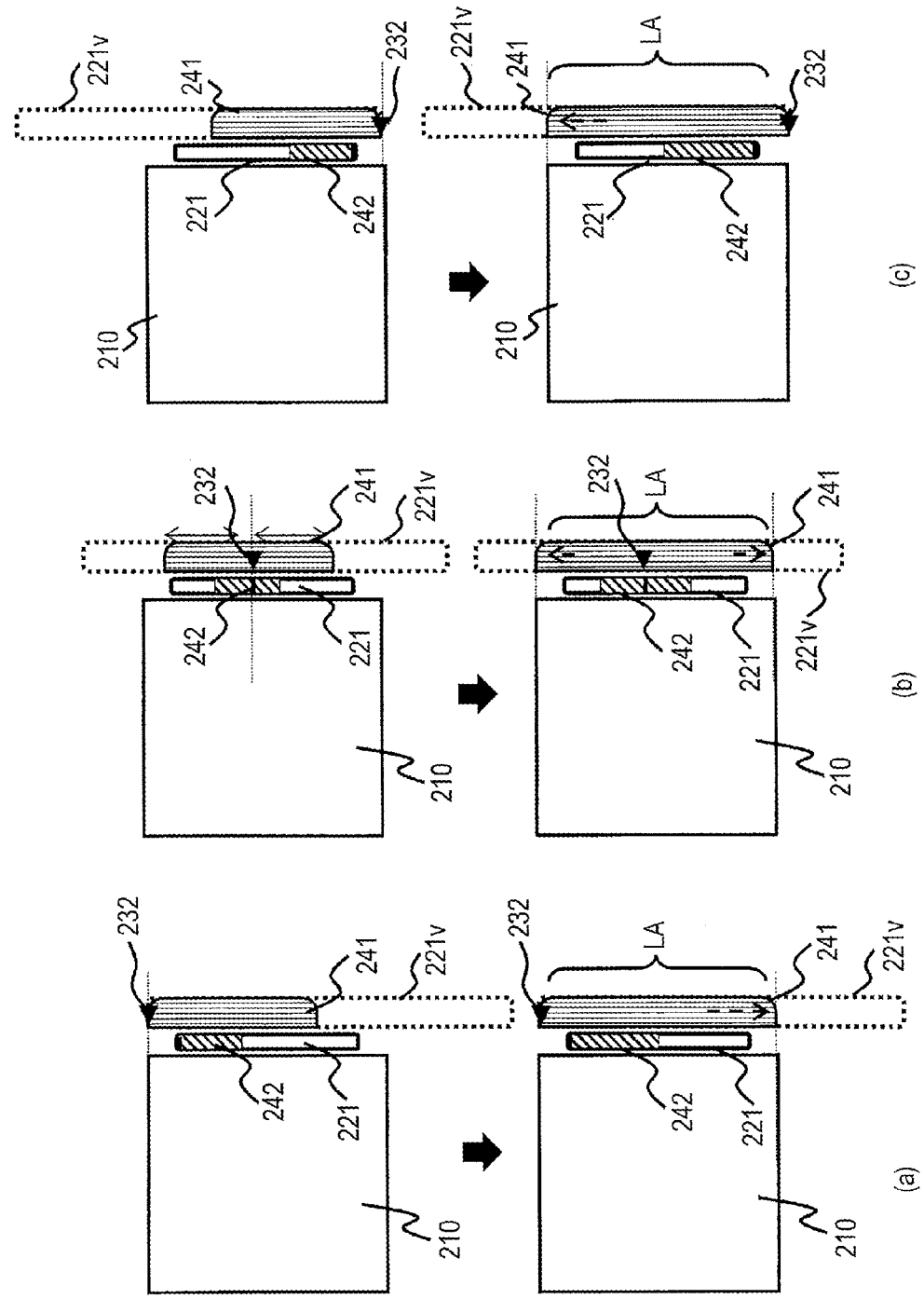
[FIG.13]

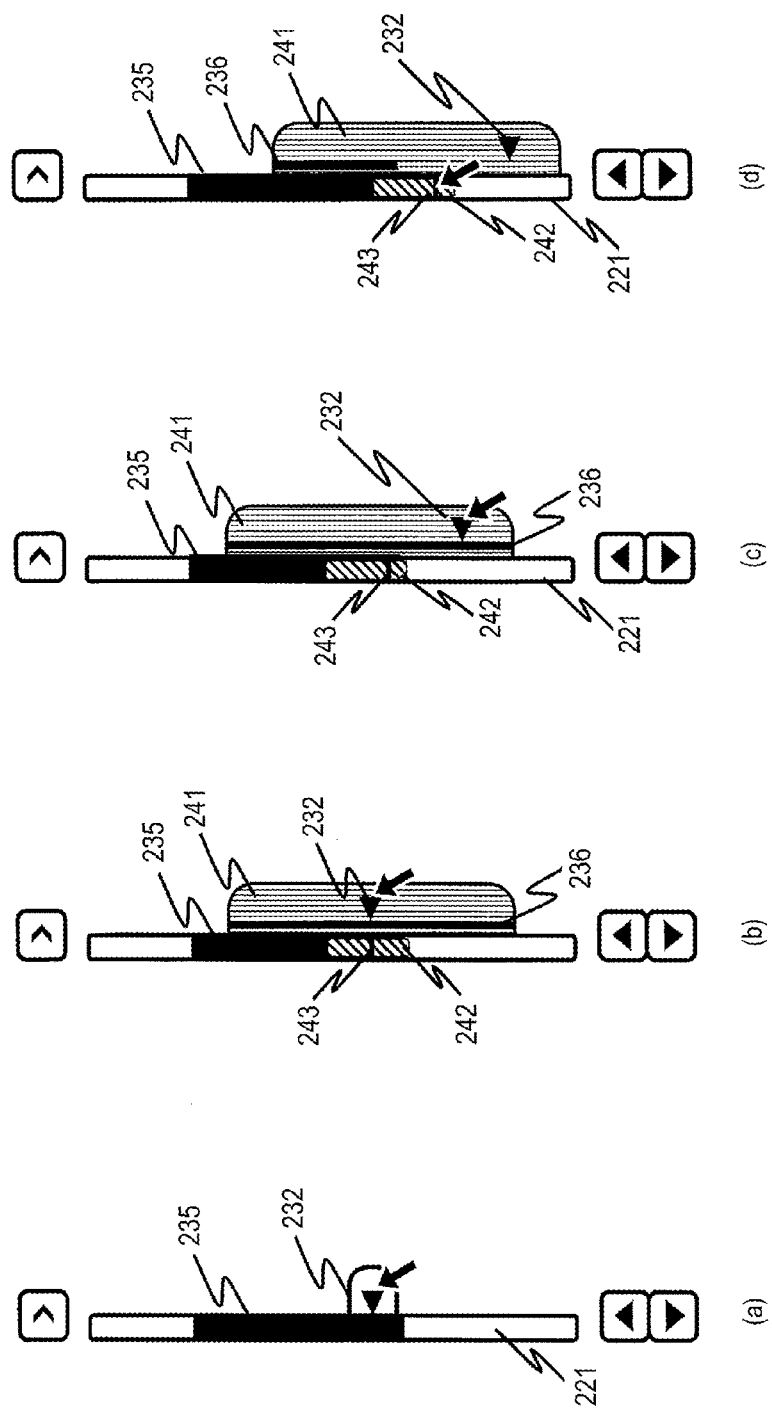

[FIG.15]
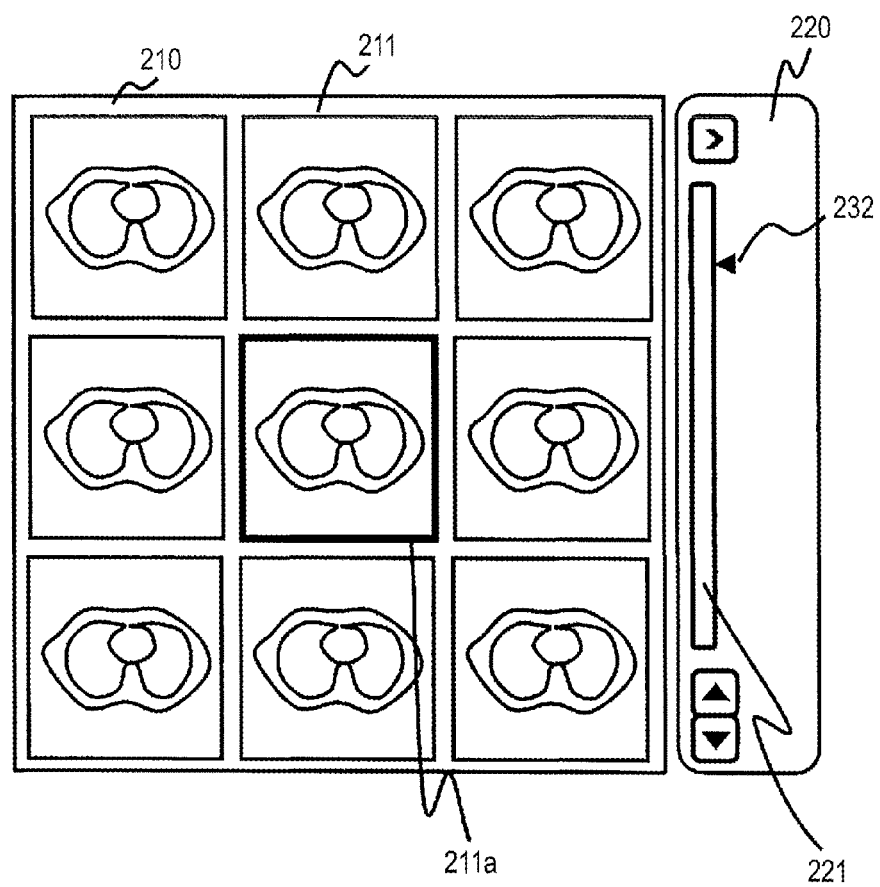

[FIG.16]
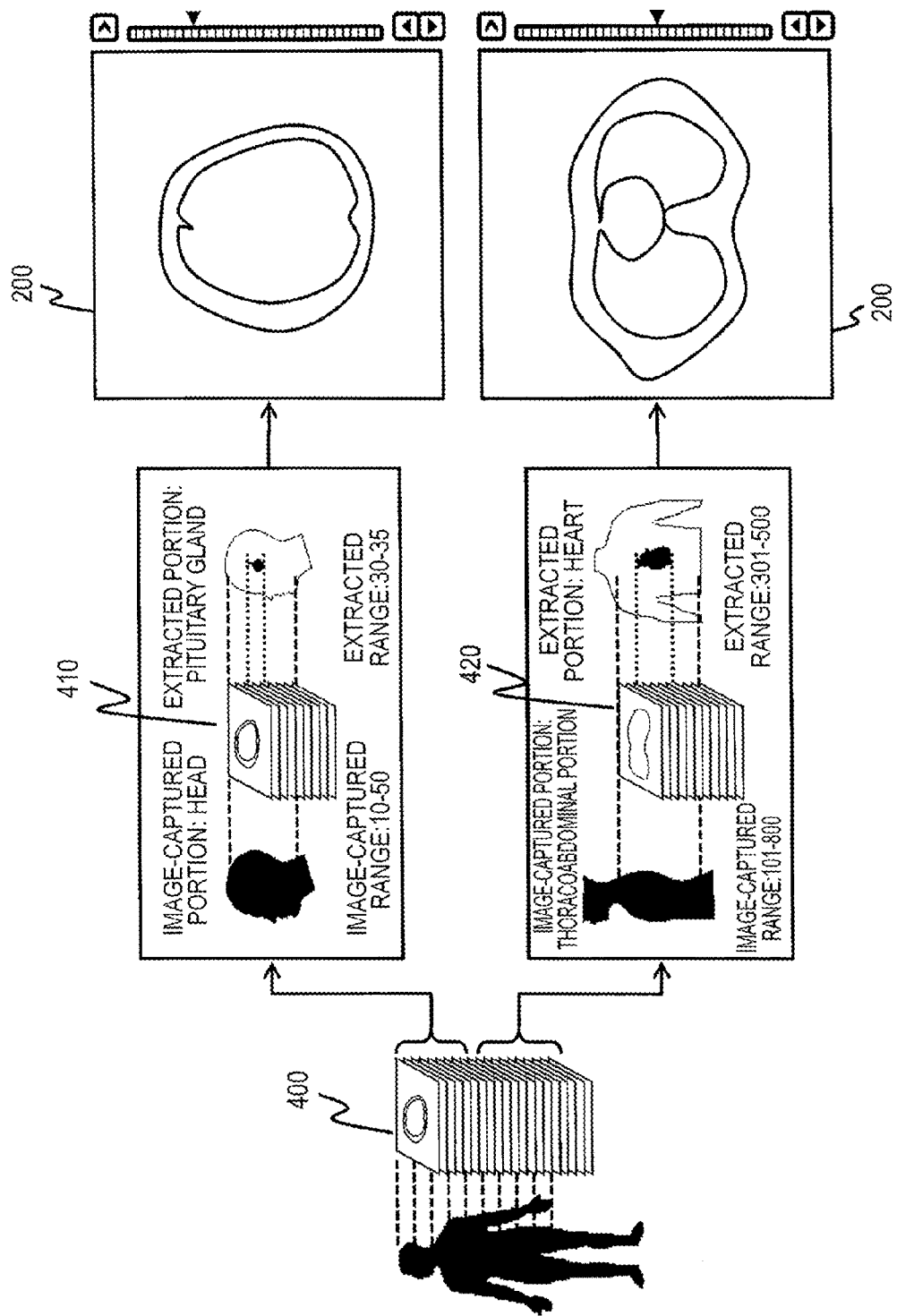

[FIG.17]
| No. | IMAGE-CAPTURED PORTION | IMAGE-CAPTURED RANGE [slice] | EXTRACTED PORTION | EXTRACTED RANGE [slice] | REPRESENTATIVE POSITION [slice] | NUMBER OF IMAGES TO BE FED [slice] | FEED SPEED [slice/s] |
|---|---|---|---|---|---|---|---|
| 1 | HEAD | 11-15 | PITUITARY GLAND | 30-35 | 32 | 2 | 2 |
| 2 | THORACOABDOMINAL PORTION | 101-800 | HEART | 301-500 | 400 | 3 | 5 |
(a)
500
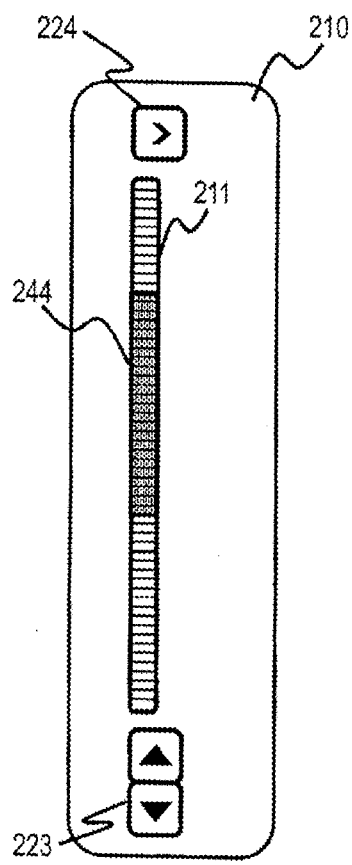
(b)

[FIG.18]
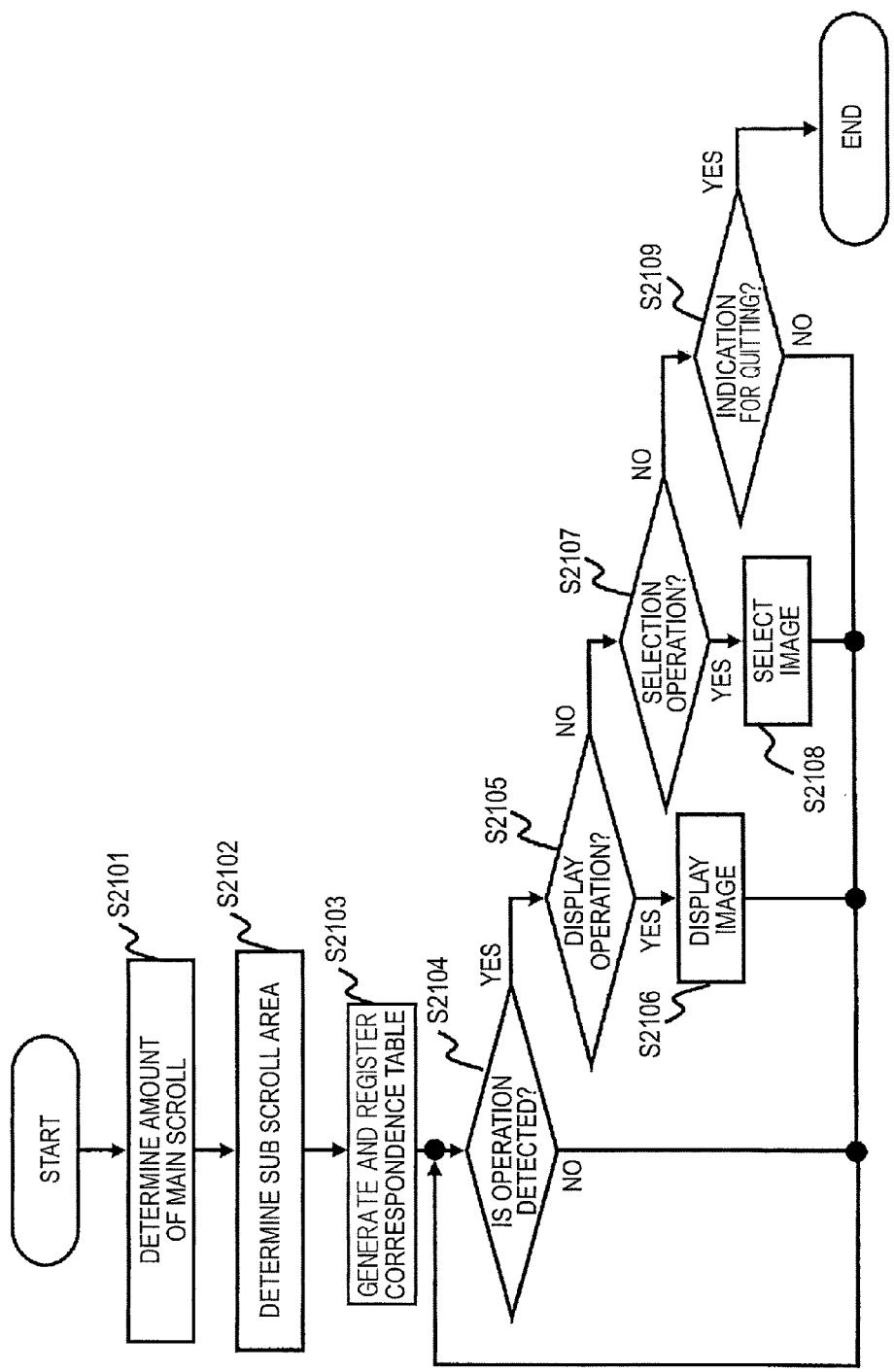

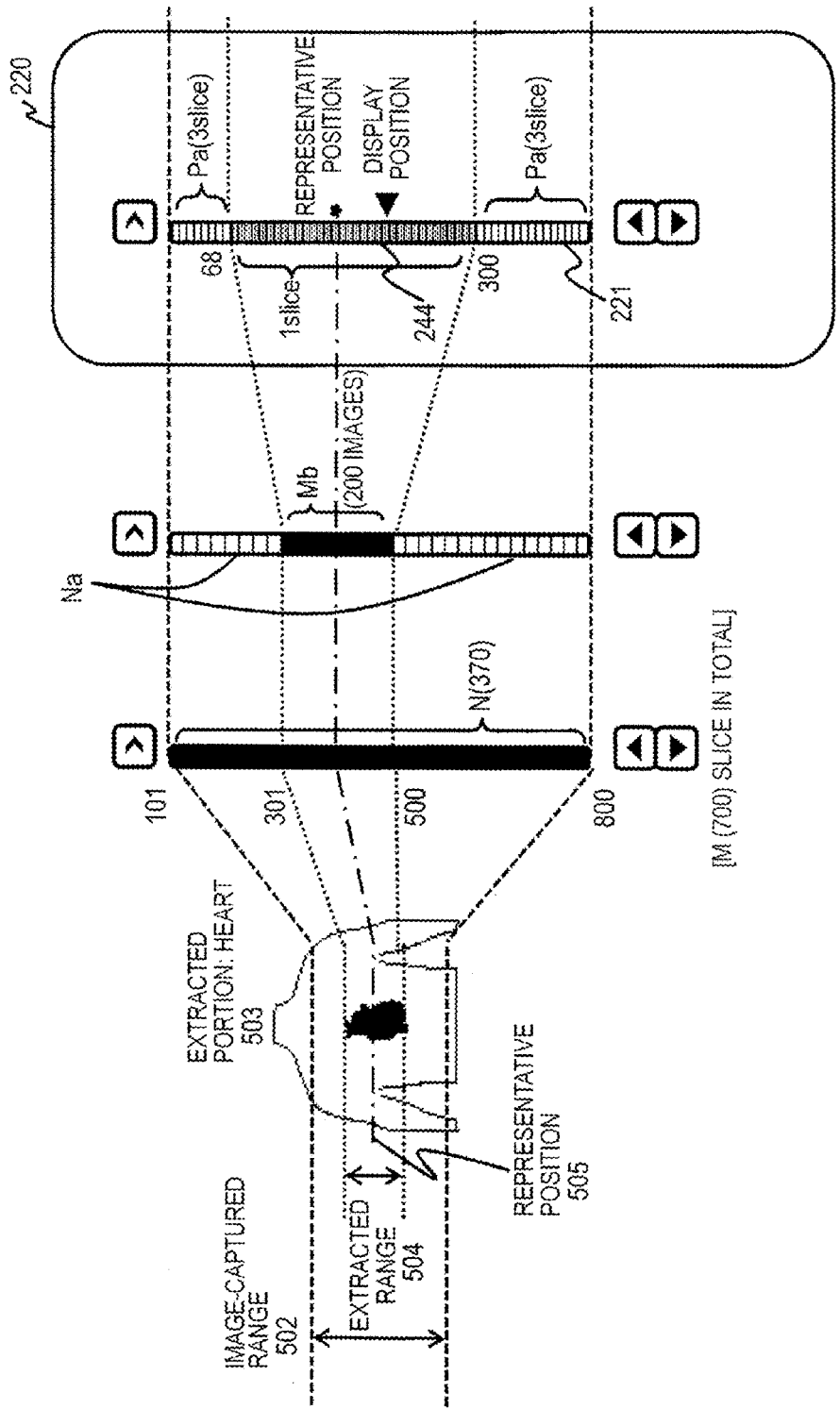
[FIG.19]

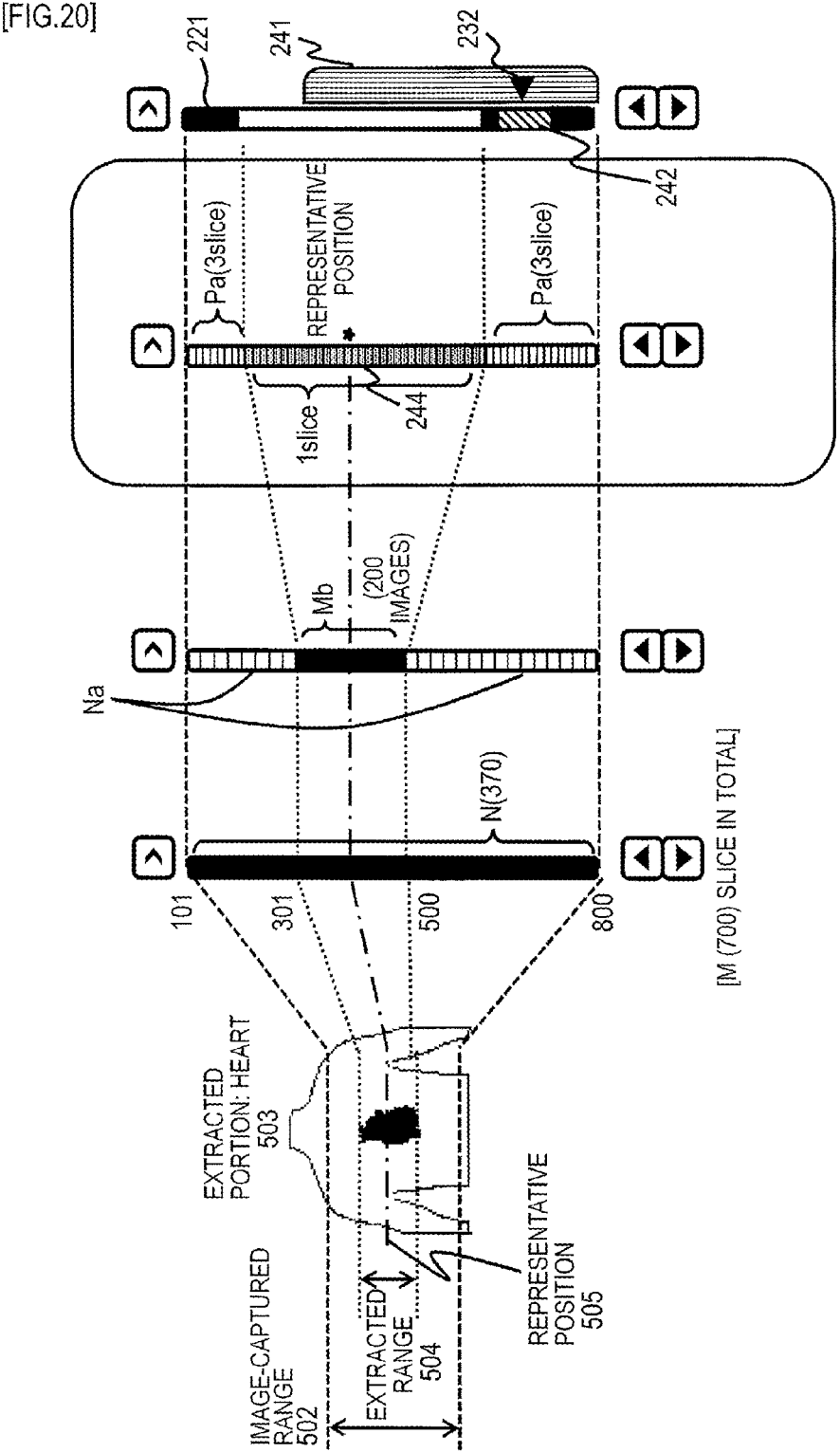

[FIG.21]

| No. | IMAGE-CAPTURED PORTION | IMAGE-CAPTURED RANGE [slice] | EXTRACTED PORTION | EXTRACTED RANGE [slice] | NUMBER OF IMAGES TO BE FED OUT OF EXTRACTED RANGE [slice] | NUMBER OF IMAGES TO BE FED IN EXTRACTED RANGE [slice] |
|---|---|---|---|---|---|---|
| 1 | HEAD | 11-15 | PITUITARY GLAND | 30-35 | 5 | 2 |
| 2 | THORACOABDOMINAL PORTION | 101-800 | HEART | 301-500 | 6 | 3 |

SYSTEM AND METHOD FOR IMAGE DISPLAY CONTROL

TECHNICAL FIELD

The present invention relates to a display control technology for display of a large quantity of continuous images. In particular, the present invention relates to a display control technology that supports a user in selectively extracting an image of interest from among a large quantity of continuous images.

BACKGROUND ART

The progress of a CT device, an MRI device, and the like increases the number of image data (also including a video) such as 3-dimensional image data or time-series 2-dimensional image data which can be acquired at one inspection. At the time of a diagnosis, it is necessary to select and extract an image of interest for a detailed browsing from among a large quantity of the images.

For example, there is a technology in which a thumbnail image or the like is used to more efficiently select an image of interest (for example, refer to Patent Document 1). A large quantity of images is divided into several image groups, and a representative image of each of the image groups is referred to as the thumbnail image. In the technology in Patent Document 1, first, ranges are approximately set, thumbnail images for image data in the set ranges are displayed on a display device, and selection of the image of interest is received via the displayed thumbnail images.

However, when the thumbnail image is used, a display area is greatly compressed. It is not possible to take a general look at all the acquired images, and it is also difficult to understand a position of a display image in all the images.

In order to avoid such an inconvenience, there is a technology in which an image of interest is selected while scrolling images to be displayed in the display area by using a scroll function. A scroll area (scroll bar) receiving a scroll operation is sequentially assigned to each of the images at equal intervals, and based on a scroll by a user, the images allotted to positions are displayed in an image display area. The user sees the images displayed in the image display area, and selects an image of interest.

PRIOR ART REFERENCES

Patent Documents

[PATENT DOCUMENT 1] Japanese Patent Unexamined Publication (KOKAI) No. 2010-234068

DISCLOSURE OF THE INVENTION

Object to be Achieved by the Invention

When the scroll function is used, the user can select the image of interest while substantially browsing the images. The user can take a general look at all the images, and easily grasp a position of the display image in all the images. However, when the number of images is equal to or greater than the number of dividable scroll areas, there are images that the user cannot select even with the minimum unit of a scroll. In this case, it is not possible to feed and confirm the images in a single unit.

The present invention is made in consideration of the problems, and an object of the present invention is to provide a technology that supports a user in easily selecting an image of interest from among a large quantity of continuous images while making the best use of characteristics of a scroll function.

Means for Achieving the Object

The present invention prepares a first scroll area that receives an indication for sequentially scrolling images to be displayed on a display screen among the large quantity of continuous images by a predetermined first amount of a scroll; and a second scroll area that receives an indication for sequentially scrolling the images by the amount of a scroll smaller than the first amount of a scroll, in a case where the number of the continuous images is greater than the maximum number of designatable positions of the first scroll area.

For example, an image display control device that controls display of a display target image group configured to have a plurality of continuous images on a display device includes sub scroll area generation means for generating a sub scroll area in which the images can be scrolled by a desired amount of a scroll, in a case where the total number of images of the display target image group is greater than the maximum number of designatable positions of a main scroll area that receives a scrolling indication for a display image; and display control means for displaying the image of the display target image group on the display device based on a scrolling indication received via either the main scroll area or the sub scroll area. In the image display control device, the amount of a scroll is defined as the number of images that are fed when an indicating position moves between the designatable positions by one step.

Provided is an image display control method for displaying a display target image group configured to have a plurality of continuous images on a display device. The method includes a display control step of changing the amount of a scroll to a desired amount of a scroll, and then of scrolling the images, in a case where the total number of images of the display target image group is greater than the maximum number of designatable positions of a main scroll area that receives a scrolling indication for a display image.

Effect of the Invention

According to the present invention, it is possible to support a user in easily selecting the image of interest from among the large quantity of continuous images while making the best use of characteristics of a scroll function.

BRIEF DESCRIPTION OF DRAWINGS

FIG. 1(a) is a diagram illustrating a configuration of a medical image display system of a first embodiment, and FIG. 1(b) is a block diagram of a medical image display device of the first embodiment.

FIG. 2 is a function block diagram of an image display control device of the first embodiment.

FIG. 3 is a view describing an example of a display screen of the first embodiment.

FIG. 4(a) is a view describing the number of designatable positions of main selectors of the first embodiment. FIG. 4(b) is a view describing the total number of images of a display target image group of the first embodiment.

FIGS. 5(a) to 5(d) are views describing each state of the display screen of the first embodiment.

FIGS. 6(a) and 6(b) are examples of a main selector correspondence table of the first embodiment.

FIG. 7 is an example of a sub selector correspondence table of the first embodiment.

FIGS. 8(a) and 8(b) are views describing display positions and display procedures of a sub selector of the first embodiment.

FIG. 9 is a flow chart of a display control process of the first embodiment.

FIG. 10 is a flow chart of a number of images excessing process of the first embodiment.

FIGS. 11(a) and 11(b) are views describing another example of display of the sub selector of the first embodiment.

FIG. 12 is a view describing another example of an operation of the sub selector of the first embodiment.

FIGS. 13(a) to 13(c) are views describing another example of the operation of the sub selector of the first embodiment.

FIGS. 14(a) to 14(d) are views describing another example of the display of the sub selector of the first embodiment.

FIG. 15 is a view describing another example of an image display area of the first embodiment.

FIG. 16 is a view describing a display target image group of a second embodiment.

FIG. 17(a) is an example of attribute data of the second embodiment. FIG. 17(b) is a view describing main selector and sub selector areas of the second embodiment.

FIG. 18 is a flow chart of an excess amount-of-images process of the second embodiment.

FIG. 19 is a view describing a method of determining the amount of a main scroll and a sub selector area of the second embodiment.

FIG. 20 is a view describing another example of display of a sub selector of the second embodiment.

FIG. 21 is a view describing attribute data of a third embodiment.

MODES FOR CARRYING OUT THE INVENTION

Hereinafter, a first embodiment of the present invention will be described. In all the drawings for describing embodiments, the same reference numerals are assigned to elements having the same functions, and repeated descriptions thereof will be omitted.

<<First Embodiment>>

In an embodiment, a sub scroll area is provided in which a different amount of a scroll is applied based on an indication from a user. First, a configuration of an entire medical image display system including a medical image display device of the embodiment will be described with reference to FIG. 1. FIG. 1(a) is a view illustrating the configuration of the entire medical image display system of the embodiment.

A medical image display system 100 is a system by which a doctor or the like browses and interprets a medical image of a subject such as a patient image-captured by a medical imaging technologist to diagnose diseases. The medical image display system 100 is provided with one or more medical image capture devices 113, one or more servers 112, one or more medical image display devices 111, and a network 114 such as an in-hospital LAN for connection thereof.

The medical image capture device 113 is a device by which a patient's specific region is image-captured to acquire a medical image, and an MRI device, an X-ray CT device, an X-ray imaging device, or the like can used as the medical image capture device 113.

The server 112 associates the medical image acquired by the medical image capture device 113 with supplementary information including information on the subject, information of the image-capturing target region and the like, and the server 112 manages the medical image associated with the supplementary information as a medical database (image DB). A medical image group acquired by capturing a series of predetermined images is taken as a unit of the medical image, and each medical image group together with supplementary information is managed as an image file. For example, a plurality of continuous image groups are multiple slice images acquired by image-capturing a 3-dimensional area, a video configured to have a plurality of continuous frames, or the like. For example, a unit, in which the medical image group is managed, is set to be one medical inspection or the like.

The supplementary information includes information of an image-capturing target subject (for example, the name of the subject, an identification code that specifies the subject, and the like), information on a medical inspection (for example, information that specifies an acquired medical image capture device, an image-captured region, and the like), image attribute information (for example, the total number of images of an image file and the like), and the like.

The medical image display device 111 acquires medical image groups, which continue in a predetermined unit, and supplementary information from the server 112 or directly from the medical image capture device 113, and displays the medical image groups and the supplementary information to a user. For example, a unit of acquiring the medical image group is a unit image file.

Subsequently, the medical image display device 111 of the embodiment will be described in detail. FIG. 1(b) is a block diagram illustrating a configuration of an entire medical image display device 111 of the embodiment. As illustrated in FIG. 1(b), the medical image display device 111 of the embodiment is provided with an image display control device 130, a display device 128 such as a display, and an input device 129 such as a keyboard and a mouse.

The image display control device 130 is provided with an arithmetic device (CPU) 121, a main memory device (main memory) 122, an auxiliary memory device 123, a display output interface (display output IF) 124, an input interface (input IF) 125, a network adaptor (NA) 126, and a bus 127 for connection thereof. The display device 128 is connected to the display control device 130 via the display output IF 124 and the input device 129 is connected to the image display control device 130 via the input IF. The image display control device 130 is connected to the network 114 via NA 126.

The image display control device 130 of the embodiment controls display of a large quantity of continuous images (display target image group), which are display targets, on the display device 128, and supports a user in selecting and detailed browsing a desired image. For this reason, the image display control device 130 provides a user with a main scroll area that receives an indication for scrolling images in a sequence and by a predetermined amount of a scroll, and with a sub scroll area that receives an indication for scrolling the images in a sequence and by the amount of a scroll (the amount of a sub scroll) smaller than the amount of a scroll (the amount of a main scroll) of the main scroll area in a case where the total number of the images (the total number of images) contained in the display target image group is greater than the maximum number of designatable positions of the main scroll area.

In order to realize the aforementioned feature, as illustrated in FIG. 2, the image display control device 130 of the embodiment is provided with a display screen generation unit 131, a main scroll amount calculation unit 132, a sub selector generation unit 133, a display control unit 134, and a selection receipt unit 135.

When the arithmetic device 121 uploads a program pre-stored on the auxiliary memory device 123 or the like on the main memory device 122, and executes the program, a function of each unit of the image display control device 130 is realized.

The display screen generation unit 131 generates and displays a display screen on the display device 128. The display screen is generated by using image data pre-stored on the auxiliary memory device 123 or the like. The display screen generated by the display screen generation unit 131 of the embodiment will be described. FIG. 3 is a view describing an example of a display screen 200 that the display screen generation unit 131 of the embodiment initially generates when a process starts.

The display screen 200 of the embodiment is provided with an image display area 210 in which an image is displayed, and an indication receipt area 220 that receives an indication for the image displayed in the image display area 210. The indication receipt area 220 of the embodiment is provided with a main selector 221 and a display position mark movement area 222. The display control unit 134 displays a pointer 231, a display position mark 232, a thumb 233, and the like in the indication receipt area 220 to illustrate a position of an indication from a user. The pointer 231 is displayed at a position that a user indicates via the input device 129 such as a mouse and a keyboard. The pointer 231 is displayed even in an area other than the displaying area on the display screen 200.

In addition to the aforementioned configuration elements, the indication receipt area 220 may include an image feeding button 223 that receives an indication for displaying images of the display target image group in the image display area 210 one by one and in a sequence, a setting menu display button 224 that receives a selection of various processes prepared in advance, and the like.

The main selector 221 and the display position mark movement area 222 are main scroll areas that receive an indication for scrolling an image displayed in the image display area 210 by a predetermined amount of a scroll. In the embodiment, the scroll of the image displayed in the image display area 210 is realized by moving the pointer 231 on the main selector 221, or by moving the thumb 233 in the display position mark movement area 222.

Based on a scrolling indication received via the main scroll area such as the main selector 221, the display control unit 134 to be described later scrolls the display target image group in a stored sequence and by a predetermined amount of a scroll, and displays an image in the image display area 210.

A minimum value of a detectable amount of movement in the direction of the scroll on the main selector 221 is referred to as a unit step. That is, as illustrated in FIG. 4(a), positions (designatable positions), which can be designated by the pointer 231, are provided in a row in the main selector 221 in a scale of a unit step from an end portion thereof. For example, the unit step is one pixel. In the embodiment, the amount of a scroll is the number of continuous images of the display target image group, which are fed when a position indicated by the pointer 231 moves by one unit step. By the amount of a scroll, each image of the display target image group is displayed in a sequence in the image display area 210.

For example, the display control unit 134 generates in advance the correspondence table in which each designatable position of the main selector 221 is stored corresponding to each image of the display target image group, and realizes a scroll display by displaying an image in the image display area 210 with reference to the correspondence table. As described later, the main scroll amount calculation unit 132 generates the correspondence table.

The display position mark 232 illustrates a designatable position of the main selector 221, which corresponds to the image displayed in the image display area 210 at the time. For example, in the embodiment, the display position mark 232 is displayed in a flank of the main selector 221.

The main selector 221 of the embodiment discriminably displays a range of an image for which the selection receipt unit 135 receives an indication for a selection.

Herein, each display mode of the indication receipt area 220 based on an operation of a user will be described with reference to FIG. 5. In FIG. 5, a frame for illustrating the indication receipt area 220 is not illustrated.

FIG. 5(a) illustrates a display mode in a case where a display is normal. During the normal display, the main selector 221 and the display position mark 232 are displayed, and the main selector 221 receives a scroll indication for an image.

FIG. 5(b) illustrates an indication display mode in a case where a predetermined operation is carried out and another tag is displayed on the display position mark 232. Herein, FIG. 5(b) illustrates a case where the thumb 233 is displayed as the other tag. For example, the predetermined operation is a mouse over operation or the like. A user can indicate the operation by using the thumb 233.

At this time, the display screen 200 may be configured to display a menu from which an executable process is selected by the operation of the thumb 233, and to receive a selection by the user. For example, the executable process is a process of feeding image, cine display or the like. The cine display displays the images scrolling by the predetermined number of images to be fed (the amount of a scroll).

Furthermore, at this time, the display screen 200 may be configured to display an attribute information tab 234 for displaying attribute data of an image displayed in the image display area 210.

FIG. 5(c) illustrates a display mode when a predetermined scroll operation is carried out. Herein, FIG. 5(c) illustrates a case where a click and drag operation of the knob 232 is carried out as the predetermined scroll operation. The drag operation of the knob 232 is carried out in the display position mark movement area 222. Based on the amount and a position of movement of the knob 232, an image displayed in the image display area 210 changes.

FIG. 5(d) illustrates a display mode when the selection receipt unit 135 receives selection. As illustrated in FIG. 5(d), when the selection receipt unit 135 receives an indication for selecting an image, an area in the main selector 221, which corresponds to the selected image, is displayed as a selection range 235 and in a discriminable mode. For example, the discriminable mode is a mode in which the selection range 235 is displayed in a color different from other areas.

The main scroll amount calculation unit 132 of the embodiment will be described. The main scroll amount calculation unit 132 of the embodiment calculates the amount of a scroll of the main selector 221 as the amount of a main scroll. Based on a calculated result, the main scroll amount calculation unit 132 generates a correspondence table in which each image of the display target image group corresponds to each designatable position on the main selector 221, and registers the correspondence table on the auxiliary memory device 123 or the like.

In the embodiment, as illustrated in FIG. 4(a), the maximum number of designatable positions of the main selector 221 is N (N is an integer that is equal to or greater than 1), and as illustrated in FIG. 4(b), the total number of images of the display target image group is M (M is an integer that is equal to or greater than 1). As described above, in the scroll operation, the entire scroll area is divided at approximately equal intervals, and each of the equally divided areas is assigned to each image that is a scroll target. The main scroll amount calculation unit 132 of the embodiment determines the amount of a scroll by using the maximum number N of designatable positions and the total number M of images.

In a case where the total number M of images is greater than the maximum number N of designatable positions (M>N), for example, the amount P of a main scroll is calculated from the following equation (1).

$$P=\text{ABS}|\text{INT}(-M/N)| \quad (1)$$

Herein, INT (x) is a function that returns the maximum integer which does not exceed x, and ABS (x) is a function that returns an absolute value of x.

In a case where the total number M of images is equal to or smaller than the maximum number N of designatable positions (M≤N), the main scroll amount calculation unit 132 determines the number (step width) Q of unit steps that move in order to feed one image, and generates a correspondence table based on a determined result. For example, the step width Q is calculated from the following equation (2).

$$Q=\text{INT}(N/M) \quad (2)$$

For example, in a case where an initial value of the number of images to be fed (the amount of a main scroll) or a step width is predetermined, the number of images to be fed may change from the initial value and be calculated in such a manner that a percentage of the number of images to be fed is equal to or less than 100%. For example, the percentage of the number of images to be fed is a value acquired when the number of images to be fed is subtracted from the total number M of images, a resultant value of the subtraction is then subtracted from the maximum number N of designatable positions, and then a resultant value of the second subtraction is multiplied by 100.

Herein, a correspondence table for a main selector (a main selector correspondence table) generated by the main scroll amount calculation unit 132 will be described. FIG. 6(a) illustrates an example of a main selector correspondence table 310 generated by the main scroll amount calculation unit 132 in a case where the total number M of images is greater than the maximum number N of designatable positions (M>N), and the amount P of a main scroll is calculated to be 2. FIG. 6(b) illustrates an example of a main selector correspondence table 320 in a case where the total number M of images is equal to or smaller than the maximum number N of designatable positions (M≤N), and the number Q of unit steps is calculated to be 3.

As illustrated in FIGS. 6(a) and 6(b), in the main selector correspondence tables 310 and 320, each of designatable positions on the main selector 221 correspond to, respectively, images of the display target image group. A position number 301 is assigned to each of the designatable positions in series from the end portion of the main selector 221. A unique image number 302 is sequentially assigned to each of the images of the display target image group. Herein, FIGS. 6(a) and 6(b) illustrate a case where position numbers 301 correspond to image numbers 302.

The display control unit 134 to be described later specifies the position number 301 based on a detected position of the pointer 231, and displays the image specified by the corresponding image number 302 in the image display area 210.

As illustrated in FIG. 6(a), in a case where the total number M of images is greater than the maximum number N of designatable positions (M>N), a plurality of continuous images (herein, two images) are assigned to the same designatable position. As illustrated in FIG. 6(b), when the total number M of images is equal to or smaller than the maximum number N of designatable positions (M≤N), the same image is assigned to a plurality of continuous designatable positions (herein, three designatable positions).

Subsequently, the sub selector generation unit 133 of the embodiment will be described. In a case where the total number M of images is greater than the maximum number N of designatable positions (M>N), the sub selector generation unit 133 generates a sub selector based on an indication from a user. The sub selector is a sub scroll area that receives an indication for displaying the display target image group in the image display area 210 in a stored sequence and by a predetermined amount of a scroll (the number of images to be fed for each designatable position). Similarly to the main selector 221, the sub selector is an interface that receives an indication for an image that is selected from the display target image group and is displayed in the image display area 210.

Specifically, the sub selector generation unit 133 generates a correspondence table (sub selector correspondence table) in which images of the display target image group correspond to, respectively, designatable positions of the sub selector, and displays the sub selector in the indication receipt area 220. The sub selector generation unit 133 carries out the process whenever the sub selector generation unit 133 receives an indication for generating the sub selector from a user. For example, the indication for generating the sub selector is carried out by a mouse over operation in which the pointer 231 on the main selector 221 is moved to an outside thereof, and the displayed thumb 233 is clicked. The generated sub selector correspondence table is registered on the auxiliary memory device 123 or the like.

The amount of a scroll of the sub selector (the amount of a sub scroll) is equal to or smaller than the amount of a main scroll, and is predetermined. In the embodiment, the amount (the number of images to be fed for each unit step) of a scroll of the sub selector is 1. In the embodiment, the maximum number of designatable positions of the sub selector is predetermined. In the embodiment, the maximum number of designatable positions of the sub selector is L (L is an integer that is equal to or greater than 1 and equal to or smaller than N).

A procedure, in which the sub selector generation unit 133 generates the sub selector correspondence table, will be described. When the sub selector generation unit 133 receives an indication for generating the sub selector, the sub selector generation unit 133 extracts an L number of continuous images centered about an image displayed (a display image) in the image display area 210 at the time from the display target image group, and generates a sub selector correspondence table in which the continuous images correspond to, respectively, an L number of designatable positions of the sub selector. The display image is assigned to the center of the designatable positions of the sub selector. At the same time, the position numbers 301 of the main selector 221 also correspond to, respectively, the images assigned to the designatable positions.

FIG. 7 illustrates an example of a sub selector correspondence table 330 that is generated at the time. Herein, FIG. 7 illustrates a case where when the sub selector generation unit 133 receives an indication for generating the sub selector, an image number of a display image is Mp, the maximum number L of designatable positions of the sub selector is an odd number, and the amount P of a main scroll is 2.

In the sub selector correspondence table 330, the L number of images centered about the current display image Mp, are registered in association with each designatable position 303 of the selector, respectively in order. An image of the image number Mp is registered in association with a center sub selector position (position number: (L+1)/2), and images of the image numbers Mp −1 to Mp −(L−1)/2 are registered in association with sub selector position numbers (L+1)/2−1 to 1, respectively in order. Images of the image numbers Mp +1 to Mp +(L−1)/2 are registered in association with sub selector position numbers (L+1)/2+1 to L, respectively in order.

For example, in a case where the maximum number L of designatable positions is an even number, instead of (L+1)/2, L/2 is used as the position number of the center sub selector position.

Even with the sub selector, the display control unit 134 to be described later specifies the position number 301 in the sub selector correspondence table based on a detected position of the pointer 231, and displays the image specified by the corresponding image number 302 in the image display area 210.

Subsequently, a display position and a display procedure of the sub selector will be described with reference to FIG. 8.

As illustrated in FIG. 8(a), in a state where the thumb 233 is displayed, when it is detected that the thumb 233 is selected and clicked by the pointer 231, the sub selector generation unit 133 displays a sub selector 241 in the indication receipt area 220. As illustrated in FIG. 8(b), at this time, the sub selector generation unit 133 displays the sub selector in such a manner that the center position in a vertical direction (in a scroll direction) of the sub selector 241 aligns with a position of the display position mark 232. As described in the generation of the sub selector correspondence table 330, this is because the display image Mp corresponds to the center designatable position in the sub selector 241, and the display position mark 232 indicated a position on the main selector 221, which corresponds to the display image Mp.

For example, as illustrated in FIG. 8(b), the sub selector 241 is displayed at a position adjacent to the main selector 221.

At this time, the sub selector generation unit 133 may be configured to discriminably display a sub selector area 242 in an area of the main selector 221, and the sub selector area 242 corresponds to the range of an image which can receive a scrolling indication via the sub selector 241. With reference to the sub selector correspondence table 330 previously generated, the sub selector generation unit 133 specifies both end portions of the position number 301, and displays the sub selector area 242.

Similarly to the display position mark 232, while the sub selector 241 is displayed, the display control unit 134 may be configured to display a line 243 on the main selector 221 at a position that corresponds to the display image, on the main selector 221.

In a case where the sub selector generation unit 133 detects that the pointer 231 moves to another operation area of the indication receipt area 220, the sub selector generation unit 133 deletes display of the sub selector 241 from the indication receipt area 220, and the sub selector correspondence table 330 from a registration destination such as the auxiliary memory device 123. For example, the other operation areas include the main selector 221, the image feeding button 223, the setting menu display button 224, and the like.

Subsequently, the display control unit 134 of the embodiment will be described. The display control unit 134 of the embodiment controls display of images of the display target image group in the image display area 210. Specifically, when a user specifies the display target image group, the main scroll amount calculation unit 132 calculates the amount of a main scroll. When the sub selector generation unit 133 receives an indication for generating the sub selector, the display control unit 134 commands the sub selector generation unit 133 to generate the sub selector. When the display control unit 134 receives an indication for a scroll or the like via any one of the main selector 221, the display position mark movement area 222, the sub selector 241, or the like, based on the received indication, the display control unit 134 displays an image in the image display area 210. When the selection receipt unit 135 receives an indication for selection, the selection receipt unit 135 carries out a selection process.

An image displayed in the image display area 210 is determined based on the main selector correspondence tables 310 and 320, and the sub selector correspondence table 330. A receipt of an indication is carried out by detecting the position of the pointer 231. Based on a detected position of the pointer 231, the display control unit 134 determines a correspondence table to be referenced. With reference to the determined correspondence table, the display control unit 134 specifies the position number 301 based on a detected position of the pointer 231, and displays the image specified by the corresponding image number 302 in the image display area 210. For example, the detected position of the pointer 231 and the position number in the correspondence table are related to each other by coordinate values of a coordinate system of the indication receipt area 220.

In a case when the total number M of images is greater than the maximum number N of designatable positions (M>N), a plurality of the images are made to correspond to one of the designatable positions. In this case, as per a predetermined rule, a display image is determined from among the images that correspond to the designated position. For example, the predetermined rule indicates that an image assigned with the minimum image number is displayed, an image assigned with a medium image number is displayed, or the like.

As describe above, whenever an image is displayed in the image display area 210, the display control unit 134 refers to a correspondence table, and displays the display position mark 232 at a position that corresponds to the display image. In a case where the sub selector 241 is displayed, the line 243 is also displayed. Based on the sub selector area 242 and the line 243 which are displayed by the sub selector generation unit 133, a user can grasp where an image displayed in the image display area 210 is positioned in all the images.

Subsequently, the selection receipt unit 135 of the embodiment will be described. The selection receipt unit 135 of the embodiment receives selection of an image by a user, and selects the received image. In the embodiment, the selection receipt unit 135 receives selection of an image for detailed browsing from the display target image group. In the embodiment, in a case where the selection receipt unit 135 receives a predetermined operation, an image displayed in the image display area 210 at the time is to be selected. For example, the predetermined operation is an operation of clicking the display image, a click and drag operation on the main selector 221, or the like.

For example, when an image desired to be selected is displayed in the image display area 210, a user clicks the image in the image display area 210. When the selection receipt unit 135 receives the operation, the selection receipt unit 135 makes the image turn to a selected state. When a predetermined range of the main selector 221 is selected by a click and drag operation, the selection receipt unit 135 makes an image group that corresponds to the range turn to a selected state. For example, the selection is realized when a selection flag is affixed to correspond to an image number of a selected image in each correspondence table.

For example, when an image desired to be selected is displayed in the image display area 210, a user clicks the image in the image display area 210. When the selection receipt unit 135 receives the operation, the selection receipt unit 135 makes the image in a selected state. When a predetermined range of the main selector 221 is selected by a click and drag operation, the selection receipt unit 135 makes an image group that corresponds to the range in the selected state. For example, the selected state is realized by affixing a selection flag in association with an image number of a selected image in each correspondence table.

When the selection receipt unit 135 receives the same process to the images in the selected state, the selection receipt 135 of the embodiment releases the selected state of the images.

In the embodiment, the display target image group is acquired from the server 112 or the medical image capture device 113, and is registered on the auxiliary memory device 123 or the like. The display process, the selection process and the like are carried out on the image group registered on the auxiliary memory device 123 or the like. However, if supplementary information of images necessary for each of the processes, for example, the total number of images and the like can be acquired, the display target image group may not be necessarily registered on the image display control device 130. The image display control device 130 may be configured to have direct access to a storage destination such as the server 112 and acquire the display target image group via the NA 126.

Subsequently, a flow of a display control process by the display control unit 134 of the embodiment will be described. FIG. 9 is a process flow of the display control process of the embodiment. The following display control process starts upon receiving an indication for a process start and/or selection of the display target image group (image file) from a user. The display screen 200 is generated in advance, and is displayed on the display device 128.

First, the display control unit 134 compares the total number M of images contained in the display target image group with the maximum number N of designatable positions of the main selector 221 (step S1101). The maximum number N of designatable positions of the main selector 221 is predetermined. The total number M of images of the display target image group is acquired from supplementary information of the display target image group.

As a result of the comparison, in a case where the total number M of images is equal to or smaller than the maximum number N of designatable positions (M≤N), the display control unit 134 commands the main scroll amount calculation unit 132 to generate the correspondence table 320 (step S1102). Using the equation (2), the main scroll amount calculation unit 132 calculates the number Q of unit steps, generates the main selector correspondence table 320, and registers the main selector correspondence table 320 on the auxiliary memory device 123.

Until the display control unit 134 receives an indication for quitting from the user, the display control unit 134 carries out a normal image display process. Herein, the display control unit 134 detects operations of the pointer 231 and the like by the user (step S1103). Until the display control unit 134 receives an indication for quitting from the user (step S1104), the detection is repeated at predetermined time intervals. Based on the detected operation, the display control unit 134 carries out the following process.

If the detected operation is an operation (display operation) of indicating image display (step S1105), the display control unit 134 displays an image in the image display area 210 (step S1106). For example, as described above, the display operation is an operation in which the pointer 231 is placed at a predetermined position on the main selector 221, and the pointer 231 is moved on the main selector 221. At this time, based on the detected position of the pointer 231 on the main selector 221, the display control unit 134 displays the image in the image display area 210 with reference to the main selector correspondence table 320.

If the detected operation is an operation (selection operation) of receiving an indication for image selection (step S1107), the selection receipt unit 135 receives selection of an image, and carries out a selection process (step S1108). For example, as described above, the selection operation is a double click operation or a drag and draw operation. With reference to the main selector correspondence table 320, the selection receipt unit 135 selects an image indicated by the operation, or an image group that corresponds to an indicated range.

If the detected operation is an indication for quitting (step S1104), the display control unit 134 exits the process. In a case where any operation is not detected, or the detected operation is not related to any case, the display control unit 134 returns to step S1104, and waits to detect the next operation.

In contrast, as a result of step S1101, in a case where the total number M of images is greater than the maximum number N of designatable positions (M>N), the display control unit 134 carries out an number of images excessing process to be described later (step S1109).

Hereinafter, a flow of the number of images excessing process by the display control unit 134 of the embodiment will be described with reference to FIG. 10. In the number of images excessing process, based on an operation of the pointer 231 by the user, with reference to the main selector correspondence table 310, the display control unit 134 displays an image, or receives the selection operation. In a case where a predetermined indication for generating the sub selector is detected, the display control unit 134 displays the sub selector 241, and receives an indication for a display image on the sub selector 241.

First, the display control unit 134 commands the main scroll amount calculation unit 132 to determine the amount P of a main scroll, and to generate the correspondence table 310 (step S1201). For example, using the equation (1), the main scroll amount calculation unit 132 calculates the amount P of a main scroll, and generates the main selector correspondence table 310 illustrated in FIG. 6(a) by using the calculated amount P of a main scroll, and registers the main selector correspondence table 310 on the auxiliary memory device 123.

Subsequently, the display control unit 134 detects operations of the pointer 231 and the like (step S1202). Until the display control unit 134 receives an indication for quitting (step S1212), the detection is repeated at predetermined time intervals. Based on the detected operation, the display control unit 134 carries out the following process.

If the detected operation is the display operation (step S1203), the display control unit 134 displays an image in the image display area 210 similarly to in the normal image display process (step S1204). For example, the display operation includes various operations of the main selector 221, the sub selector 241, the display position mark movement area 222, and the like. As per a predetermined rule, a display image is extracted from images registered in the main selector correspondence table 310 or the sub selector correspondence table 330, in order to correspond to a position indicated by the pointer 231. Herein, when the display operation is detected on the main selector 221 or in the display position mark movement area 222, a display image is extracted with reference to the main selector correspondence table 310. When the display operation is detected on the sub selector 241, a display image is extracted with reference to the sub selector correspondence table 330.

If the detected operation is the selection operation (step S1205), the selection receipt unit 135 receives selection of an image similarly to in the normal image display process (step S1206).

If the detected operation is an operation of displaying the sub selector 241 (SS display operation) (step S1207), the display control unit 134 commands the sub selector generation unit 133 to generate the sub selector correspondence table (SS correspondence table) 330 (step S1208), and to display the sub selector (SS) 241 (step S1209). For example, as illustrated in FIG. 8(a), the SS display operation is an operation in which the thumb 233 is clicked in a state where the thumb 233 is displayed on the display position mark 232. The sub selector generation unit 133 registers the generated sub selector correspondence table 330 on the auxiliary memory device 123.

If the detected operation is an indication (SS display-finishing indication) for finishing display of the sub selector (step S1210), the display control unit 134 deletes the sub selector (SS) 241 (step S1211). For example, as described above, the sub selector display-finishing indication means a case where it is detected that the pointer 231 moves to another operation area of the indication receipt area 220.

If the detected operation is an indication for quitting (step S1212), the display control unit 134 exits the process. In a case where any operation is not detected, or the detected operation is not related to any case, the control unit returns to step S1202, and waits to detect the next operation.

As described above, the image display control device 130 of the embodiment is the image display control device 130 that controls display of the display target image group configured to have the continuous images on the display device 128. The image display control device 130 is provided with the sub selector generation unit 133 that generates the sub scroll area (sub selector 241) in which the images can be scrolled by a desired amount of a scroll, in a case where the total number of images of the display target image group is greater than the maximum number of designatable positions of the main scroll area (main selector 221) that receives the scrolling indication for the display image; and the display control unit 134 that displays the image of the display target image group on the display device 128 based on a scrolling indication received via either the main scroll area or the sub scroll area. In the image display control device 130 the amount of a scroll is defined as the number of images that are fed when an indicating position moves between the designatable positions by one step.

The image display control device 130 of the embodiment is further provided with the main scroll amount calculation unit 132 that calculates the amount of a main scroll which is the amount of a scroll of the main scroll area by using the total number of images and the maximum number of designatable positions, in a case where the total number of images is greater than the maximum number of designatable positions.

The main scroll area is generated on the display screen 200 on which the image is displayed. The sub scroll area is generated in an area on the display screen, and is an area independent from the main scroll area. The sub selector generation unit 133 generates the sub scroll area whenever receiving an indication from a user. Whenever the sub selector generation unit 133 generates the sub scroll area, the sub selector area 242 is discriminably displayed in the main scroll area. The sub selector area 242 is the range of the designatable position of the main scroll area, and corresponds to the range of the image designated in the sub scroll area.

Accordingly, in the embodiment, there is provided the sub selector 241 through which a predetermined number of continuous images can be fed (scroll) by one image unit based on an indication from a user. The sub selector 241 can be associated with a desired range of images. Accordingly, even in a case where the total number M of images of the display target image group is greater than the maximum number N of designatable positions of the main selector 221, the user can scroll and confirm the desired range of images as one image unit.

In the embodiment, while keeping a benefit of an image display process by a scroll bar, that is, the benefit that it is possible to easily grasp the position of the image displayed in the image display area in all the images, it is possible to browse a desired range of images as one unit regardless of the number of display target images.

Accordingly, in the embodiment, it is possible to provide an intuitively easy-to-use image display control device to a user who selects an image for a detailed browsing from among a large quantity of continuous images, and to effectively support the user in the selection operation.

As an example, the embodiment describes a case where the sub selector 241 is disposed in such a manner that a position of the center thereof coincides with the position of the display position mark 232, but the present invention is not limited to the case. For example, as illustrated in FIG. 11(a), in a case where an indication for displaying the sub selector is carried out when the display position mark 232 is positioned in a range from an upper end of the main selector 221 to a half (L/2) of the maximum number L of designatable positions of the sub selector 241, the sub selector 241 may be displayed at a position different from the embodiment described above. In this case, for example, as described in FIG. 11(b), the sub selector 241 is displayed in such a manner that an upper end of the sub selector 241 coincides with the upper end of the main selector 221. In this case, the sub selector area 242 is also displayed to coincide with the display position of the sub selector 241.

Similarly, even in a case where the display position mark 232 is positioned in a range from a lower end of the main selector 221 to L/2, the sub selector 241 may be configured in such a manner that a lower end of the sub selector 241 coincides with the lower end of the main selector 221.

In the embodiment, the image display process is carried out only in a case where the pointer 231 is detected on either the main selector 221 or the sub selector 241 during display of the sub selector 241, but the present invention is not limited to the configuration.

For example, in a case where a predetermined operation is carried out in an area that is outside the sub selector 241 and is in the vicinity of an end portion of the sub selector 241 during display of the sub selector 241, the display control unit 134 may be configured to sequentially display images before and after L numbers images registered in the sub selector correspondence table 330.

For example, specifically, as illustrated in FIG. 12, in a case where the pointer 231 is disposed in an area in the vicinity of the upper end of the sub selector 241, and a click operation or the like is carried out, based on the number of click, the display control unit 134 may be configured to move up and display the images in the image display area 210 sequentially from the image immediately before the L numbers images registered in the sub selector correspondence table 330. Similarly, even in a case where the pointer 231 is disposed in an area in the vicinity of the lower end of the sub selector 241, and the same operation is carried out, based on the number of click, the display control unit 134 may be configured to feed and display the images in the image display area 210 sequentially from the image immediately after the images registered in the sub selector correspondence table 330.

At this time, similarly to in the above description, the line 243 is displayed at a position that corresponds to the image displayed in the image display area 210 and is registered in the main selector correspondence table 310.

In the embodiment, the maximum number (the length of the sub selector) of designatable positions of the sub selector 241 is constant. However, the maximum number of designatable positions of the sub selector 241 may be variable.

When a predetermined sub selector expansion-and-contraction operation is received, the display control unit 134 commands the sub selector generation unit 133 to execute the sub selector expansion-and-contraction operation. For example, the predetermined expansion-and-contraction operation is an operation in which the end portion of the sub selector 241 is indicated by the pointer 231, and is dragged up to a desired length. For example, when the pointer is detected in the end portion of the sub selector 241, the display control unit 134 may be configured to display an adjustment tool for adjusting the length of the sub selector, and to adjust the length via the adjustment tool.

After the expansion-and-contraction operation is received and executed, the sub selector generation unit 133 detects the maximum number LA of designatable positions of the sub selector 241, and regenerates the sub selector correspondence table 330 by using the detected maximum number LA of designatable positions. At the time of the regeneration, on the basis of a display image at the time and a position that corresponds to the display image, images increase and decrease by an increased and decreased number of the designatable positions in a direction where the sub selector 241 increases and decreases.

For example, in a case where the length of the sub selector 241 expands by 3 unit steps, the sub selector 241 increases by 3 unit steps in an expansion direction, and is displayed. Continuous images increased by 3 unit steps are additionally registered in the sub selector correspondence table 330. On the contrary, in a case where the length of the sub selector 241 contracts by 3 unit steps, the sub selector 241 decreases by 3 unit steps in a contraction direction, and is displayed. Images are deleted from the sub selector correspondence table 330 by 3 unit steps.

As illustrated in FIG. 13(a), on the basis of the display position mark 232, in a case where the sub selector 241 expands downward, images immediately after the images registered in the sub selector correspondence table 330 before the expansion are added to the sub selector correspondence table 330 by the expanded number of designatable positions. As illustrated in FIG. 13(b), on the basis of the display position mark 232, in a case where the sub selector 241 expands upward and downward, respectively, by the same number of designatable positions, images before and after the registered images are added, respectively, in the sub selector correspondence table 330 by the expanded number of positions. As illustrated in FIG. 13(c), similarly, in a case where the sub selector 241 expands upward, images immediately after the registered images are added by the expanded number of designatable positions.

In FIGS. 13(a) to 13(c), areas outside the sub selector 241 illustrated by dotted lines are virtual main selector areas 221v. The virtual main selector area 221v is an area for the number of positions, which is necessary when all the images of the display target image group is designated as the number of images to be fed being 1. That is, the virtual main selector area 221v is an area for the number M of designatable positions. The sub selector 241 is expandable to the virtual main selector area 221v, but in the embodiment, the expandable length is limited to the maximum number N of designatable positions of the main selector. Display of the sub selector area 242 displayed on the main selector 221 expands in synchronization with the expansion of the sub selector 241.

The sub selector generation unit 133 may be configured to receive an indication from a user and to be able to move the display position of the sub selector 241 displayed in the indication receipt area 220 as per the procedure.

In a state where the sub selector 241 and the sub selector area 242 are displayed, when the display control unit 134 receives a drag operation for the sub selector 241, the display control unit 134 commands the sub selector generation unit 133 to move the display position of the sub selector 241 in synchronization with the drag operation. At this time, whenever the sub selector 241 is displayed at a new position, the sub selector generation unit 133 updates the sub selector correspondence table 330, and also moves the sub selector area 242 on the main selector 221.

For example, the sub selector generation unit 133 carries out the update by specifying a designatable position of the main selector 221, which corresponds to the center of the sub selector 241 after the movement, and taking an image corresponding to the position in the main selector correspondence table 310 as an image of the designatable position for the center of the sub selector 241.

The embodiment illustrates a configuration in which a selected range is discriminably displayed on the main selector 221 in a case where the selection receipt unit 135 receives selection of an image for a detailed browsing, but the present invention is not limited to the configuration. For example, as illustrated in FIGS. 14(b) to 14(d), in a case where selection is done before the sub selector 241 is displayed, the embodiment may be configured to discriminate a designatable position of the sub selector 241, which corresponds to images contained in the selected range. Each of FIGS. 14(*b*) to 14(*d*) illustrates a case where a bold line is displayed at a position of the sub selector, which corresponds to the images in a selected state.

For example, as illustrated in FIG. 14(*a*), the selection range 235 is set on the main selector 221. As illustrated in FIG. 14(*b*), in a case where the selection range 235 includes the sub selector area 242 on the main selector 221, since the sub selector 241 selects all the images that receive a scroll indication, a bold line 236 is displayed at all the designatable positions of the sub selector 241. For example, as illustrated in FIG. 14(*c*), even in a case where the sub selector 241 moves according to the method, when the selection range 235 includes the entire sub selector area 242 that corresponds to the sub selector 241 after the movement, the bold line 236 is displayed in the same manner.

For example, when the sub selector 241 moves, a target image group to which the sub selector 241 receives an operation changes due to the movement. In this case, the bold line 236 is displayed in only an area that corresponds to images in the selection range 235. The display position of the bold line 236 is determined with reference to the sub selector correspondence table 330.

The embodiment illustrates a configuration in which one of the images designated in the indication receipt area 220 is displayed in the image display area 210, but the present invention is not limited to the configuration. For example, as illustrated in FIG. 15, the embodiment may be configured to display the plurality of images.

In this case, the image display area 210 is provided with a plurality of sub image display areas 211. The display control unit 134 displays an image designated in the indication receipt region 220 in a predetermined sub image display area 211*a* of the sub image display area 211, and as per a predetermined rule, sequentially displays images before and after the display image in other sub image display areas 211.

In this case, whenever the display image designated in the indication receipt area 220 changes, the display control unit 134 changes the display image in the image display area 211*a* by using the method described in the embodiment. Due to this change, the display images in the other image display areas 211 change. For example, when the pointer 231 moves on the main selector 221 or on the sub selector 241, at every detection time, the display control unit 134 displays an image corresponding to the position of the pointer at the time in the predetermined sub image display area 211*a*, and similarly as per the rule, sequentially displays images before and after the image in the other sub image display areas 211.

In the embodiment, at the time of scrolling images, a correspondence table is generated in advance for each of the main selector 221 and the sub selector 241, and with reference to the correspondence table, an image is specified to correspond to the detected position of the pointer 231, and an image to be displayed in the image display area 210 is specified. However, a method of determining the image to be displayed in the image display area 210 is not limited to the embodiment. For example, the embodiment may be configured to determine a next display image without generating the correspondence table and by using the number of images to be fed or the step width, the image number of the image displayed just before, the position of the pointer 231 at the time, and the amount of movement of the pointer 231.

<<Second Embodiment>>

Subsequently, a second embodiment of the present invention will be described. In the embodiment, images in a predetermined image range of the display target image group are scrolled by a predetermined amount of a scroll (the amount of a sub scroll) that is equal to or smaller than the amount of a main scroll. For example, from among the display target image group, an image group of a predetermined region is scrolled by the amount of a sub scroll. For example, the image range scrolled by the amount of a sub scroll is taken as an image group of a region desired to be more closely observed.

In the first embodiment, the sub selector is set independently from the main selector by an indication from a user. In the embodiment, an area of the main selector, which corresponds to a predetermined image range of a large quantity of continuous images, is taken as the sub selector that is scrolled by a predetermined amount of a scroll. Hereinafter, the embodiment will be described with primary focus on configurations different from those of the first embodiment.

The medical image display system 100 of the embodiment is basically the same as that of the first embodiment. In the embodiment, a hardware configuration of the medical image display device 111 is also the same as that of the first embodiment. In the embodiment, function blocks of the image display control device 130 are also the same as those of the first embodiment. As described above, since a sub selector generation process is different from that of the first embodiment, a function of each part is different.

In the embodiment, as described above, a predetermined image range of the display target image group is scrolled by a predetermined amount of a scroll (the amount of a sub scroll). Accordingly, in the embodiment, supplementary information of the display target image group includes information that specifies the image range which is scrolled by the amount of a sub scroll.

First, the display target image group and attribute data of the embodiment will be described. The attribute data of the supplementary Information is a database in which information in use for processes of the embodiment is stored.

FIG. 16 is a view describing the display target image group of the embodiment. As illustrated in FIG. 16, a captured image group 400 captured at one inspection includes a plurality of image-captured regions. Herein, FIG. 16 illustrates a case where the captured image group 400 includes a head image group 410 and a thoracoabdominal image group 420. In the embodiment, the image group for each of the image-captured regions is taken as the display target image group when a process is carried out.

FIG. 17(*a*) illustrates an example of an attribute data 500 of the captured image group 400. As the attribute data 500, an image-captured range 502, an extracted region 503, an extracted range 504, a representative position 505, and a number of images to be fed 506 for each an image-captured region 501 are stored. As illustrated in FIG. 17(*a*), a feed speed 507 used in cine display may be further stored.

As the image-captured range 502, information that specifies the image groups corresponding to the regions by unique image numbers (slice numbers) that are sequentially assigned to all the images of the captured image group 400 is stored. For example, as the attribute data 500 illustrated in FIG. 17(*a*), in case the image-captured region is a head region (the head image group 410), information of slices 11 to 50 is stored, and in case the image-captured region is a thoracoabdominal region (the thoracoabdominal image group 420), Information of slices 101 to 800 is stored.

Among the image-captured regions, a name of a region desired to be scrolled by a predetermined amount of a scroll is registered in the extracted region 503. For example, the pituitary gland is registered for the head image group 410, and the heart is registered for the thoracoabdominal image group 420.

Information that specifies images (slices) corresponding to the extracted region 503 is registered in the extracted range 504. For example, information of slices 30 to 35 is stored for the head image group 410, and information of slices 301 to 500 is stored for the thoracoabdominal images. As the representative position 505, information that specifies a representative slice of each of the extracted regions is stored.

The maximum allowable number of images to be fed of the images in the extracted range is registered in the number of images to be fed 506. For example, in a case where the number of images to be fed of the images in the extracted range is predetermined to be 1, the number of images to be fed 506 may not be registered. Hereinafter, the embodiment illustrates a case where the number of images to be fed of the images in the extracted range is set to be 1.

As the feed speed 507, the number of images to be fed per 1 second, when an indication for cine display or the like is received and the display target image group is automatically scroll displayed, is stored.

In the embodiment, the total number of images of the image group specified in the extracted range 504 does not exceed the maximum number N of designatable positions of the main selector 221.

Subsequently, in the embodiment, a function of each part of the image display control device 130 will be described. Processes of the display screen 131 and the selection receipt unit 135 of the embodiment are basically the same as those of the first embodiment.

Similarly to in the first embodiment, the main scroll amount calculation unit 132 of the embodiment calculates the amount of a scroll of the main selector 221 as the amount of a main scroll. Based on a calculated result, the main scroll amount calculation unit 132 generates a correspondence table in which each of designatable positions of the main selector 221 corresponds to each image of the display target image group, and registers the correspondence table on the auxiliary memory device 123 or the like.

With reference to the attribute data 500, the main scroll amount calculation unit 132 of the embodiment extracts the total number M of images of the display target image group. The total number M of images is calculated by using the information of the image-captured range 502. Similarly to in the first embodiment, the total number M of images is compared to the maximum number N of designatable positions of the main selector 221. In a case where the total number M of images is equal to or smaller than the maximum number N of designatable positions (M≤N), it is possible to display all the images in the image display area 210 by scrolling the main selector 221. Accordingly, it is not necessary to set the sub selector, and to display a predetermined area by a desired amount of a scroll.

For this reason, similarly to in the first embodiment, in a case where the total number M of images is equal to or smaller than the maximum number N of designatable positions (M≤N), the main scroll amount calculation unit 132 calculates the number (step width) Q of unit steps for feeding one image, for example, from the following equation (2), and based on a calculated result, generates the sub selector correspondence table 320.

In the extracted range, the images may be scrolled by the number of images to be fed designated in the attribute data.

In a case where the total number M of images is greater than the maximum number N of designatable positions (M>N), processes of calculating the amount of a main scroll and generating the main selector correspondence table 310 by the main scroll amount calculation unit 132 will described later.

In a case where the total number M of images is greater than the maximum number N of designatable positions (M>N), the sub selector generation unit 133 of the embodiment generates the sub selector. The sub selector receives an indication for displaying the images of the extracted range of the display target image group in the image display area 210 in a stored sequence and by a predetermined amount of a scroll (the number of images being fed per one designatable position, and in the embodiment, 1).

As illustrated in FIG. 17(b), in the embodiment, the sub selector is generated on the main selector 221. That is, a predetermined area of the main selector 221 is taken as the sub selector. Hereinafter, the area of the main selector 221 set as the sub selector is referred to as a sub selector area 244. A process of determining the sub selector area 244 will be described in detail.

The display control device 134 of the embodiment controls display of the images of the display target image group in the image display area 210. In the embodiment, for example, when a user specifies the display target image group, the display control device 134 commands the main scroll amount calculation unit 132 to calculate the amount of a main scroll. The display control unit 134 commands the sub selector generation unit 133 to determine the sub selector area 244 on the main selector. Based on an indication received via the display screen 200, the display control unit 134 displays an image in the image display area 210, and commands the selection receipt unit 135 to be set the image in a selected state.

Herein, a display control process by the display control unit 134 of the embodiment will be described. The display control process by the display control unit 134 of the embodiment is basically the same as the display control process of the first embodiment illustrated in FIG. 9. In a case where the total number M of images is greater than the maximum number N of designatable positions (M>N), a number of images excessing process is different from that of the first embodiment.

Hereinafter, the number of images excessing process of the embodiment will be described. In the embodiment, in the number of images excessing process, first, the main scroll amount calculation unit 132 and the sub selector generation unit 133 determine the number of images to be fed for each of the designatable positions of the main selector 221, and generate the main selector correspondence table 310. Hereinafter, with primary focus on the process of generating the main selector correspondence table, the number of images excessing process of the embodiment will be described with reference to FIGS. 18 and 19. FIG. 18 is a process flow of the number of images excessing process of the embodiment. FIG. 19 is a view describing a method of determining the amount of a main scroll and the sub selector area of the embodiment.

First, the main scroll amount calculation unit 132 determines the amount of a main scroll by using the maximum number N of designatable positions and the attribute data (step S2101).

As illustrated in FIG. 19, in the embodiment, in a state where the number of images to be fed is set to be 1, the image group of the extracted range 504 is displayed and controlled in the sub selector area 244 set on the main selector 221. In contrast, image groups out of the extracted range are displayed and controlled in remaining areas (areas for images out of the extracted range) of the main selector 221 by the number of images to be fed determined by the main scroll amount calculation unit 132.

For example, when the total number of images of the images groups out of the extracted range is set to be Ma (Ma is an integer that satisfies a relationship of 0<Ma<M), and the maximum number of designatable positions of the images areas out of the extracted range is set to be Na (Na is an integer that satisfies a relationship of 0<Na<N), the amount Pa of a main scroll is expressed by the following equation (3).

$$Pa=\mathrm{ABS}|\mathrm{INT}(-Ma/Na)| \quad (3)$$

Herein, the total number Ma of images out of the extracted range is expressed by Ma=M−Mb, in which M is the total number of images, and Mb (Mb is an integer that satisfies a relationship of 0<Mb<M) is the total number of images of the extracted range. The maximum number Na of designatable positions of the image areas out of the extracted range is expressed by Na=N−Nb, in which N is the maximum number of designatable positions, and Nb (Nb is an integer that satisfies a relationship of 0<Nb<N) is the maximum number of designatable positions that is used when the images of the extracted range are fed. In the embodiment, the number of images to be fed of the extracted range is set to be 1.

Accordingly, since Nb=Mb, when the equation (3) is expressed by using the maximum number N of designatable positions which is a predetermined value, and the total number M of images and the total number Mb of images of the extracted range which are acquired as the attribute data 500, the equation (3) is restated by the following equation (4).

$$Pa=\mathrm{ABS}|\mathrm{INT}(-(M-Mb)/(N-Mb))| \quad (4)$$

By using the maximum number N of designatable positions, the attribute data 500, and the equation (4), the main scroll amount calculation unit 132 of the embodiment calculates the amount Pa of a main scroll, that is, the number of images to be fed for the images out of the extracted range.

For example, in the attribute data of the thoracoabdominal image group, the image range includes an image having an image number of 101 through an image having an image number of 800, the total number M of images is 700, the extracted region is the heart, the extracted range includes an image having an image number of 301 through an image having an image number of 500, the total number Mb of images of the extracted region 200, and the representative image is a 401th image. In a case where the image group is taken as the display target image group, and the maximum number N of designatable positions is 370, the amount Pa of a main scroll is three images.

Subsequently, the sub selector generation unit 133 receives a result from the main scroll amount calculation unit 132, and determines the sub selector area 244 on the main selector 221, of which display is controlled by the amount of a sub scroll (step S2102). In the embodiment, the amount of a sub scroll is acquired by setting the number of images to be fed per one step to 1.

Based on the number of images other than the extracting target images, and the amount Pa of a main scroll, the sub selector generation unit 133 determines a position of one end portion of the sub selector area 244, of which an image number is smaller than that of the extracting target image group. The sub selector generation unit 133 determines a position of the other end portion of the sub selector area 244 by using the total number Ma of images of the extracting target image group. For example, as illustrated in FIG. 19, in the thoracoabdominal image group 420 having the attribute data 500, the number of images before the extracting target image group is 200. The number of images to be fed other than the extracting target images is 3. Accordingly, 67 steps are used for non-extracted images before the extracting target images. The sub selector area 244 is determined as an area of a 68th designatable position to a 300th designatable position.

When the amount Pa of a main scroll and the sub selector area 244 are determined, the main scroll amount calculation unit 132 generates the main selector correspondence table 310 in which each image corresponds to each designatable position of the main selector, and registers the main selector correspondence table 310 on the auxiliary memory device 123 or the like (step S2103).

Similarly to in the first embodiment, even in the embodiment, in a case where an initial value of the amount of a main scroll (the number of images to be fed) is predetermined, the amount of a main scroll may change from the initial value, and be calculated in such a manner that a percentage of the number of images to be fed is equal to or less than 100%.

Thereafter, until the display control unit 134 receives an indication for quitting from a user at predetermined time intervals (step S2109), the display control unit 134 detects operations of the pointer 231 and the like by the user (step S2104).

If the detected operation is a display operation (step S2105), the display control unit 134 displays an image in the image display area 210 (step S2106). The display operation is the same as that of the first embodiment. If the detected operation is a selection operation (step S2107), the display control unit 134 commands the selection receipt unit 135 to receive selection of an image, and to carry out a selection process (step S2108). The selection operation is the same as that of the first embodiment.

If the detected operation is an indication for quitting (step S2109), the display control unit 134 exits the process. Ina case where any operation is not detected, or the detected operation is not related to any operation, the display control unit 134 returns to step S1204, and waits to detect the next operation.

As described above, the image display control device 130 of the embodiment is the image display control device 130 that controls display of the display target image group configured to have a plurality of the continuous images on the display device. The image display control device 130 is provided with the sub selector generation unit 133 that generates the sub scroll area (sub selector area 244) in which the images can be scrolled by a desired amount of a scroll, in a case where the total number of images of the display target image group is greater than the maximum number of designatable positions of the main scroll area (main selector 221) that receives the scrolling indication for the display image; and the display control unit 134 that displays the image of the display target image group on the display device based on a scrolling indication received via either the main scroll area or the sub scroll area. In the image display control device 130, the amount of a scroll is defined as the number of images that are fed when an indicating position moves between the designatable positions by one step.

The image display control device 130 of the embodiment is further provided with the main scroll amount calculation unit 132 that calculates the amount of a main scroll which is the amount of a scroll of the main scroll area by using the total number of images and the maximum number of designatable positions, in a case where the total number of images is greater than the maximum number of designatable positions.

The main scroll area is generated on the display screen 200 on which the image is displayed. The display target image group includes the attribute information (attribute data 500) that has the amount of a sub scroll which is the amount of a scroll of the sub scroll area, and has information which specifies the image group which of the display target image group is scrolled by the amount of a sub scroll, as the extracted image group. The sub selector generation unit 133 generates the sub scroll area in the main scroll area based on the attribute information. The main scroll amount calculation unit 132 calculates the amount of a main scroll, taking the attribute information into consideration.

In the embodiment, the main selector is provided with the sub selector area in which the number of images to be fed of a predetermined extracted region is equal to or smaller than the maximum number of images to be fed. Accordingly, even in a case where the number of images of the display target image group is greater than the maximum number N of designatable positions of the main selector, it is possible to display and confirm the images of the extracted region in the image display area by a desired number of images to be fed. While keeping easiness of grasping all the images by using a scroll bar, it is possible to browse necessary images by a desired number of images to be fed regardless of the number of images of the display target image group.

In particular, when the maximum number of images of the extracted region is set to be 1, it is possible to browse the images of the extracted region one by one.

Accordingly, in the embodiment, it is possible to provide an intuitively easy-to-use image display control device to a user who selects an image for a detailed browsing from among a large quantity of continuous images, and to effectively support the user in the selection operation.

Even in the embodiment, in the images out of the extracted range, in a case where the number Na of unit steps for the images out of the extracted range is smaller than the number Ma of images out of the extracted range (Na<Ma), similarly to in the first embodiment, the embodiment may be configured to display the sub selector 241 as illustrated in a right end portion of FIG. 20. A generation method, a display position, an operation, and the like of the sub selector 241 are the same as those of the sub selector 241 of the first embodiment.

The embodiment illustrates an example in which the number of images to be fed of the extracted region is set to be 1, but the number of images to be fed is not limited to 1. It is possible to set the number of images to be fed to any number.

In this case, when the maximum number of images to be fed of the extracted region is set to be p (p is an integer that is equal to or greater than 1), the equation (4) is restated by the following equation (5).

$$Pa=ABS|INT(-(M-Mb)/(N-Mb/p))| \quad (5)$$

In this case, there is a case where the number of images to be fed of the area (sub selector area 244) set as the sub selector is equal to or greater than 2. Accordingly, even for the sub selector area 244, the sub selector generation unit 133 may be configured to receive the same operation as that of the first embodiment, and to generate and display the sub selector 241 in which the number of images to be fed is 1.

A generation method, a display position, an operation and the like of the sub selector 241 of the embodiment are the same as those of the sub selector 241 of the first embodiment.

The maximum number of images to be fed of the extracted region may not be supplemented to each image file as the attribute data 500. For example, the embodiment may be configured to register only a name of the extracted region in the attribute data 500, and to retain the recommended maximum number of images to be fed for a region as an independent data for a recommended number of images to be fed. In this case, for use in the process, the display control unit 134 extracts the name of the extracted region from the attribute data, and the corresponding number of images to be fed with reference to the data for a recommended number of images to be fed.

The extracted region is not limited to one continuous area of the display target image group. A plurality of the continuous areas may be set as the extracted region. That is, the image-captured region may have the plurality of extracted regions.

In a case where the sub selector 241 is generated, and is displayed beside the main selector 221, similarly to in the first embodiment, various modification processes related to the sub selector 241 such as a disposition of the sub selector 241, an expansion and contraction of the sub selector 241, a feeding of images based on an operation in an area out of the sub selector 241, a movement of the sub selector 241, and display of synchronization of the selection range are applicable to this embodiment.

Similarly to in the first embodiment, even the embodiment may display a plurality of images in the image display area 210.

<<Third Embodiment>>

Subsequently, a third embodiment of the present invention will be described. A predetermined image range of the display target image group is scrolled by the amount of a scroll that is differently set for each of the predetermined image ranges, and similarly to in the first embodiment, based on an indication from a user, the sub scroll area is provided which is scrolled by a predetermined amount of a scroll.

A medical image display system of the embodiment is basically the same as the medical image display system 100 of the first embodiment. Basically, a hardware configuration of the medical image display device of the embodiment is also the same as that of the medical image display device 111 of the first embodiment. Furthermore, basically, a functional configuration of the image display control device of the embodiment is also the same as that of the image display control device 130 of the first embodiment. In the embodiment, a function of the main scroll amount calculation unit 132 is different from that of the first embodiment.

Similarly to in the second embodiment, in the embodiment, the amount of a scroll (the number of images to be fed) is predetermined for each of predetermined image ranges of the display target image group. Accordingly, similarly to in the second embodiment, even in the embodiment, the display target image group includes the attribute data as supplementary information.

FIG. 21 is a view describing an attribute data 600 of the embodiment. Similarly to in the second embodiment, the attribute data 600 of the embodiment is provided with an image-captured range 602 for each of image-captured regions 601, an extracted region 603, and an extracted range 604. The image-captured range 602, the extracted region 603, and the extracted range 604 are configured to be the same as the likes of the attribute data 500 in the second embodiment.

Furthermore, the attribute data 600 of the embodiment is provided with a number of images to be fed in an extracted range 606 that is an initial value of the amount of a scroll (the number of images to be fed) of images in the extracted range, and a number of images to be fed out of an extracted range 605 that is an initial value of the amount of a scroll (the number of images to be fed) of images out of the extracted range.

FIG. 21 illustrates an example in which each of the display target image groups has one extracted region 603, but the embodiment may include a plurality of the extracted regions 603. In a case where the display target image group has the plurality of extracted regions 603, the attribute data 600 is provided with the extracted range 604, and number of images to be fed in an extracted range 606 for each extracted region. Similarly to in the attribute data 500 of the second embodiment, a feed speed used in cine display may be registered even in the attribute data 600 of the embodiment.

Subsequently, the main scroll amount calculation unit 132 of the embodiment will be described. In the embodiment, the main scroll amount calculation unit 132 takes into consideration a ratio of the initial values of the number of images to be fed determined in the attribute data 600, and determines the amount of a scroll of images, respectively, in the extracted range and out of the extracted range. That is, the main scroll amount calculation unit 132 of the embodiment determines the amount of a main scroll by using the maximum number N of designatable positions of the main selector 221, the number of images in the extracted range, the number of images out of the extracted range, and the initial values of the number of images to be fed thereof.

When the maximum number of designatable positions of the main selector 221 is N; the total number of images of the image group out of the extracted range is Ma; the total number of images of the image group in the extracted range is Mb; the initial value of the number of images to be fed out of the extracted range is La; the initial value of the number of images to be fed in the extracted range is Lb; and the ratio of the numbers of feed images is X, a relationship of the following equation (6) is satisfied.

$$N:(Ma/La+Mb/Lb)=1:X \qquad (6)$$

Accordingly, the ratio X of the numbers of feed images is expressed by the following equation (7).

$$X=(Ma/La+Mb/Lb)/N \qquad (7)$$

Each of N, Ma, Mb, La, and Lb is an integer that is equal to or greater than 1.

In a case where the ratio X of the numbers of feed images is equal to or less than 1, the main scroll amount calculation unit 132 of the embodiment determines the initial values La and Lb of the numbers of feed images which are registered in the attribute data 600, respectively, as the amount of a main scroll of the image group out of the extracted range, and the amount of a main scroll of the image group in the extracted range.

In contrast, in a case where the ratio X of the numbers of feed images is greater than 1, the main scroll amount calculation unit 132 determines the amounts of a main scroll of both image groups in such a manner that the ratio X of the numbers of feed images is maintained. That is, when the amount (the number of images to be fed) of a main scroll of the image group out of the extracted range is La', and the amount (the number of images to be fed) of a main scroll of the image group in the extracted range is Lb', La and Lb are calculated from, respectively, the following equations (8) and (9).

$$La'=INT(X*La) \qquad (8)$$

$$Lb'=INT(X*Lb) \qquad (9)$$

Herein, INT (x) is a function that returns the maximum integer which does not exceed x.

That is, using the equations (6) to (9), the main scroll amount calculation unit 132 of the embodiment determines the amount of a main scroll of the image group in the extracted range, and the amount of a main scroll of the image group out of the extracted range. By using information of each image range, the main scroll amount calculation unit 132 generates a correspondence table in which each designatable position of the main selector 221 corresponds to each image of the display target image group, and registers the correspondence table on the auxiliary memory device 123 or the like.

In the embodiment, in a case where not only the total number of images of the display target image group is greater than the number of designatable positions of the main selector 221 that receives a scrolling indication for a display image, but also the amount of a sub scroll (for example, 1) is smaller than both of the amounts of a main scroll in the extracted range and out of the extracted range, which are calculated by the main scroll amount calculation unit 132, the sub selector generation unit 133 generates the sub selector 241 in which images are scrolled by a desired amount of a scroll.

Other configurations of the image display control device 130 of the embodiment are basically the same as those of the first embodiment. That is, similarly to in the first embodiment, the display screen generation unit 131 generates the display screen, and displays the display screen on the display device 128. Similarly to in the first embodiment, based on a scrolling indication received at the main selector 221 or the sub selector 241, the display control unit 134 displays the display target image group on the display device. The selection receipt unit 135 receives selection of the image group from among the display target image groups.

As described above, when the number of designated positions (the number of necessary designated positions) necessary at the time of feeding images by a number of images to be fed predetermined for each region, exceeds the maximum number of designatable positions of the main selector 221, the main scroll amount calculation unit 132 of the embodiment adjusts the number of images to be fed for each region in such a manner that the number of necessary designated positions does not exceed the maximum number of designatable positions, while maintaining the ratio of the numbers of feed images predetermined for each region.

Accordingly, in the embodiment, while keeping the ratio of the predetermined numbers of feed images, it is possible to confirm the images of the extracted range and the other images. Accordingly, while confirming the images in more detail, it is possible to scroll regions of concern on the main selector. Furthermore, it is possible to browse images of a desired range one by one via the sub selector. Accordingly, it is possible to provide an intuitively easy-to-use image display control device to a user who selects an image for a detailed browsing from among a large quantity of continuous images, and to effectively support the user in the selection operation.

EXPLANATION OF REFERENCES

100: medical image display system, 111: medical image display device, 112: server, 113: medical image capture device, 114: network, 121: arithmetic device, 122: main memory device, 123: auxiliary memory device, 124: display output IF, 125: input IF, 126: NA, 127: bus, 128: display device, 129: input device, 130: image display control device, 131: display screen generation unit, 132: main scroll amount calculation unit, 133: sub selector generation unit, 134: display control unit, 135: selection receipt unit, 140: auxiliary memory device, 200: display screen, 210: image display area, 211: sub image display area, 211a: sub image display area, 220: indication receipt area, 221: main selector, 221v: virtual main selector area, 222: display position mark movement area, 223: image feeding button, 224: setting menu display button, 231: pointer, 232: display position mark, 234: attribute information tab, 235: selection range, 236: bold line, 241: sub selector, 242: sub selector area, 243: line, 244: sub selector area, 301: position number, 302: image number, 303: sub selector position number, 310: main selector correspondence table, 320: main selector correspondence table, 330: sub selector correspondence table, 400: captured image group, 410: head image group, 420: thoracoabdominal image group, 500: attribute data, 501: image-captured region, 502: image-captured range, 503: extracted region, 504: extracted range, 505: representative position, 506: number of images to be fed, 507: feed speed, 600: attribute data, 601: image-captured region, 602: image-captured range, 603: extracted region, 604: extracted range, 605: number of images to be fed out of extracted range, 606: number of images to be fed in extracted range

The invention claimed is:

1. An image display control device which comprises:
a processor;
a memory device;
a display output interface that transmits output to a display device;
an input interface that receives input from an input device;
a network adaptor connected to a network; and
a program stored on the memory device that when executed by the processor controls display of a display target image group configured to have a plurality of continuous images on the display device, wherein the program includes further instructions that cause the processor to perform the functions of:
a sub scroll area generation unit for generating a sub scroll area in which the plurality of continuous images of the display target image group can be scrolled by an amount of a scroll in the sub scroll area, in a case where a total number of images of the display target image group is greater than a maximum number of designatable positions of a main scroll area that receives a scrolling indication for a display image;
a display control unit for displaying the plurality of continuous images of the display target image group on the display device based on a scrolling indication received via either the main scroll area or the sub scroll area, wherein the amount of the scroll in the sub scroll area is defined as the number of images that are fed when an indicating position moves between the designatable positions by one step; and
a main scroll amount calculation unit for calculating an amount of a main scroll that is an amount of a scroll of the main scroll area, by using the total number of images and the maximum number of designatable positions, in a case where the total number of images is greater than the maximum number of designatable positions, wherein the main scroll area is generated on the display screen on which the image is displayed, wherein the display target image group includes stored attribute information that stores an amount of a sub scroll which is a predetermined amount of the scroll of the sub scroll area, and wherein the main scroll area further has information which specifies an image group of the display target image group, which is scrolled by the amount of a sub scroll, as an extracted image group, wherein the sub scroll area generation unit generates the sub scroll area in the main scroll area based on the attribute information, and wherein the main scroll amount calculation unit calculates the amount of a main scroll, taking the attribute information into consideration.

2. The image display control device according to claim 1, wherein the main scroll area is generated on the display screen on which the image is displayed, wherein the sub scroll area is generated in an area on the display screen, and is an area independent from the main scroll area, and wherein the sub scroll area generation unit generates the sub scroll area whenever receiving an indication from a user.

3. The image display control device according to claim 2, wherein whenever the sub scroll area generation unit generates the sub scroll area, a sub area is discriminably displayed in the main scroll area, and wherein the sub area is a range of a designatable position of the main scroll area, and corresponds to a range of an image designated in the sub scroll area.

4. The image display control device according to claim 1, wherein the display target image group is configured to have medical images of a plurality of image-capturing target regions, and wherein the extracted image group is specified by a name of an image-capturing target region in the attribute information.

5. The image display control device according to claim 1, further comprising:
a third scroll area generation unit for generating a third scroll area in which the plurality of continuous images can be scrolled by a desired amount of a scroll in an area on the display screen to be independent from the main scroll area, whenever receiving an indication from a user.

6. The image display control device according to claim 1, wherein in the amount of a sub scroll, the number of images to be fed is 1.

7. The image display control device according to claim 1, further comprising:
a selection receipt unit for receiving selection of an image from the display target image group.

8. The image display control device according to claim 7, wherein the selection receipt unit discriminably displays a designatable position of the main scroll area, which corresponds to the selected image.

9. The image display control device according to claim 1, wherein a display screen for displaying the plurality of continuous images includes a plurality of sub image display areas, on each of which one image is displayed, and wherein a display image according to the scrolling indication is displayed in a predetermined sub image display area of the plurality of sub image display areas, and images before and after the display image are displayed in other sub image display areas in a predetermined sequence.

10. The image display control device according to claim 1, wherein the plurality of continuous images of the display target image group are images acquired by a medical image acquisition device that includes at least one of the following: a magnetic resonance imaging device, an X-ray imaging device, an X-ray CT device, and an ultrasonic imaging device.

11. The image display control device according to claim 10, wherein the display target image group is either a video that has each of the plurality of continuous images as a frame or multiple slice images of a 3-dimensional area, which have each of the plurality of continuous images as a slice.

12. An image display control method for displaying a display target image group configured to have a plurality of continuous images on a display device, the method comprising:
- a sub scroll generating step of generating a sub scroll area in which the plurality of continuous images of the display target image group can be scrolled by an amount of a scroll in the sub scroll area, in a case where a total number of images of the display target image group is greater than a maximum number of designatable positions of a main scroll area that receives a scrolling indication for a display image;
- a display control step of displaying the plurality of continuous images of the display target image group on the display device based on a scrolling indication received via either the main scroll area or the sub scroll area, wherein the amount of the scroll in the sub scroll area is defined as the number of images that are fed when an indicating positions moves between the designatable positions by one step; and
- calculating, by a main scroll amount calculation unit, an amount of a main scroll that is an amount of a scroll of the main scroll area, by using the total number of images of the plurality of continuous images of the display target image group and the maximum number of designatable positions, in a case where the total number of images of the plurality of continuous images is greater than the maximum number of designatable positions, wherein the main scroll area is generated on the display device, wherein the display target image group includes stored attribute information that stores an amount of a sub scroll which is a predetermined amount of the scroll of the sub scroll area, and wherein the main scroll area further has information which specifies an image group of the display target image group, which is scrolled by the amount of a sub scroll, as an extracted image group, wherein the sub scroll area generation unit generates the sub scroll area in the main scroll area based on the attribute information, and wherein the main scroll amount calculation unit calculates the amount of a main scroll, taking the attribute information into consideration.

13. The image display control device according to claim 1, wherein the information further specifies image slices corresponding to the extracted image group.

14. An image display control device which comprises:
- a processor;
- a memory device;
- a display output interface that transmits output to a display device;
- an input interface that receives input from an input device;
- a network adaptor connected to a network; and
- a program stored on the memory device that when executed by the processor controls display of a display target image group configured to have a plurality of continuous images on the display device, wherein the program includes further instructions that cause the processor to perform the functions of:
- a sub scroll area generation unit for generating a sub scroll area in which the plurality of continuous images of the display target image group can be scrolled by an amount of a scroll in the sub scroll area, in a case where total number of images of the display target image group is greater than a maximum number of designatable positions of a main scroll area that receives a scrolling indication for a display image; and
- a display control unit for displaying the plurality of continuous images of the display target image group on the display device based on a scrolling indication received via either the main scroll area or the sub scroll area, wherein the amount of a scroll in the sub scroll area is defined as the number of images that are fed when an indicating position moves between the designatable positions by one step and the number of images is a constant integral number; and
- a main scroll amount calculation unit for calculating an amount of a main scroll that is an amount of a scroll of the main scroll area, by using the total number of images and the maximum number of designatable positions, in a case where the total number of images is greater than the maximum number of designatable positions, wherein the main scroll area is generated on the display screen on which the image is displayed, wherein the display target image group includes stored attribute information that stores an amount of a sub scroll which is a predetermined amount of the scroll of the sub scroll area, and wherein the main scroll area further has information which specifies an image group of the display target image group, which is scrolled by the amount of a sub scroll, as an extracted image group, wherein the sub scroll area generation unit generates the sub scroll area in the main scroll area based on the attribute information, and wherein the main scroll amount calculation unit calculates the amount of a main scroll, taking the attribute information into consideration.

* * * * *